(12) United States Patent
Paske

(10) Patent No.: US 6,264,621 B1
(45) Date of Patent: Jul. 24, 2001

(54) SYSTEM AND METHOD FOR PROVIDING QUANTIFIED AND QUALITATIVE HAND ANALYSIS

(75) Inventor: William C. Paske, 3331 Confederate Ct., Missouri City, TX (US) 77459-4913

(73) Assignee: William C. Paske, Sugar Land, TX (US)

(*) Notice: Subject to any disclaimer, the term of this patent is extended or adjusted under 35 U.S.C. 154(b) by 0 days.

(21) Appl. No.: 09/430,184

(22) Filed: Oct. 29, 1999

(51) Int. Cl.[7] .................................................. A61B 5/103
(52) U.S. Cl. ............................................ 600/587; 600/595
(58) Field of Search ........................... 600/587, 595, 600/592

(56) References Cited

U.S. PATENT DOCUMENTS

| | | | |
|---|---|---|---|
| 4,774,966 | 10/1988 | Lemmen | 128/774 |
| 5,002,065 | 3/1991 | LaCourse et al. | 128/739 |
| 5,157,970 | 10/1992 | Lewis, Jr. | 73/379 |
| 5,163,443 | 11/1992 | Fry-Welch et al. | 128/782 |
| 5,230,345 | 7/1993 | Curran et al. | 128/739 |
| 5,301,683 | 4/1994 | Durkan | 128/744 |
| 5,325,869 | 7/1994 | Stokes | 128/779 |
| 5,447,167 | 9/1995 | Fleischaker | 128/782 |
| 5,471,996 | 12/1995 | Boatright et al. | 128/782 |
| 5,513,651 | 5/1996 | Cusimano et al. | 128/782 |
| 5,583,201 | 12/1996 | Cameron, Sr. et al. | 530/359 |
| 5,676,157 | 10/1997 | Kramer | 128/782 |
| 5,778,885 | 7/1998 | Doyama et al. | 128/782 |
| 5,911,693 * | 6/1999 | Prochazka | 600/595 |

OTHER PUBLICATIONS

W.C. Paske, Ph.D., et al.; A Tool For Measuring Simulataneous Digital Forces: Medical Implications; Feb. 11, 1999.

* cited by examiner

*Primary Examiner*—Robert L. Nasser
*Assistant Examiner*—Pamela L Wingood
(74) *Attorney, Agent, or Firm*—Fulbright & Jaworski L.L.P.

(57) ABSTRACT

A non-invasive system and method are provided for determining the presence or absence of neural, muscular, soft tissue, bone or joint damage or other disease affecting a person's hand. A preferred system includes a plurality of digit contact members, one of which is engageable by the person's thumb and others which are engageable by other digits of the hand, at least one of the other digits being innervated by the ulnar nerve. Force detectors are operatively connected to at least two of the digit contact members for measuring the quantity of force applied to the respective digit contact members by at least one digit innervated by the median nerve and a digit innervated by the ulnar nerve, as they engage in a natural gripping motion. The measured forces may be used to calculate quality indices useful in the diagnosis of disease and the monitoring of progression of disease.

45 Claims, 31 Drawing Sheets

| $S1b_{jq}$ | $S2b_{jq}$ | $S5b_{jq}$ | $time_{jq}$ |
|---|---|---|---|
| 0.4957 | 0.3746 | 0.3682 | 18.4810 |
| 0.6677 | 0.5007 | 0.4547 | 18.4937 |
| 0.9227 | 0.6955 | 0.6023 | 18.5063 |
| 1.2903 | 1.0049 | 0.7805 | 18.5190 |
| 1.8003 | 1.4060 | 0.9994 | 18.5316 |
| 2.3696 | 1.8702 | 1.2386 | 18.5443 |
| 2.9567 | 2.3228 | 1.4931 | 18.5570 |
| 3.4666 | 2.6781 | 1.6865 | 18.5696 |
| 3.8877 | 2.9818 | 1.8392 | 18.5823 |
| 4.2138 | 3.2396 | 1.9766 | 18.5949 |
| 4.4569 | 3.3886 | 2.0683 | 18.6076 |

FIG. 15

Subject Name:   Name := "Patient Name"
Hand Tested:    Hand := "Right"
Sensor Vectors defined as: Sc-Clock; S1-Thumb; S2-Index Finger; S5-Fifth Digit Ver := "Version 1.51"
Date Tested:    Date := "Some Date"
Test No.:       Test := "S1-1"

---

System Calibrated:   Calibrated := "Last Calibration Date"

Step 1300: Read in the data file:   $M := READPRN("Pw01.cap")$

Step 1306: Break into vectors:   $Sc := M^{<3>}$   $S1 := M^{<0>}$   $S2 := M^{<1>}$   $S5 := M^{<2>}$ $$S1_0 = 14$$
$$S1_{N-2} = 15$$

$N := length(S1)$   $N = 5347$   $j := 0..N-2$

Define the time scale:   $time_j := 10 \cdot \frac{j}{790}$   $tmax := max(time)$

Step 1308: Calibrate the applied forces:

$S1b_j := S1_j \cdot 0.00593 - 0.038$   $S2b_j := S2_j \cdot 0.00573 - 0.015$   $S5b_j := S5_j \cdot 0.00509 - 0.039$

Define the "finger sum":   $Sum_j := (S2_j + S5_j)$   $Sumb_j := (S2b_j + S5b_j) \cdot \cos(30 \cdot deg)$

Step 1310: Check the Sum vs Thumb Differences:   $SumDif_j := Sumb_j - S1b_j$   $Ck := \sum SumDif_j \cdot \frac{1}{N-2}$

*FIG. 16-1A*

$CheckSum := \text{"Valid"}$  $Ck = 0.0368$ $CheckSum := if(|Ck| > |0.2|, \text{"INVALID DATA"}, \text{"Valid"})$

Step 1314: Compute The Slopes And Correlation For Each Digit Vectors:

Steps 1316 & 1318:

$SL_{sum} := slope(S1b, Sumb)$  $SL_1 := slope(S1b, S2b)$  $SL_5 := slope(S1b, S5b)$  $SL_{25} := slope(S5b, S2b)$ $r_{sum} := corr(Sumb, S1b)$  $r_1 := corr(S2b, S1b)$  $r_5 := corr(S5b, S1b)$  $r_{25} := corr(S5b, S2b)$

Steps 1320: Determine Maximum Force Per Digit Vector $s1max := max(S1b)$  $s1max = 6.1411$ $s2max := max(S2b)$  $s2max = 4.4945$ $s5max := max(S5b)$  $s5max = 2.4856$ $summax := max(Sumb)$  $summax = 6.0307$

Steps 1322: Determine Percentage Values For Each Normalized Digit Vector $S1p_j := S1b_j \cdot \dfrac{100}{s1max}$  $CorrChk := \text{"Valid"}$ $S2p_j := S2b_j \cdot \dfrac{100}{s2max}$  $CorrChk := if(r_{sum} < 0.995, \text{"INVALID CORR"}, \text{"Valid"})$ $S5p_j := S5b_j \cdot \dfrac{100}{s5max}$ $Sump_j := Sumb_j \cdot \dfrac{100}{summax}$ $N = 5347$

FIG. 16-1B

*Step 1324: Determine The Individual Force Pulse maximums  For Each Digit Vector:*

$i: 0..20 \quad T_j := tmax \cdot 0.05 \cdot i$

*Steps 1334: Calculate Exponential Fit to Thumb Force Decay Curve:*

$bT := s1max \cdot 0.30$ $npT := peak(S1b, N, time, s1max, bT)_0 \quad kt := 0..npT$ $pT := peak(S1b, N, time, s1max, bT)_1$ $TpT := peak(S1b, N, time, s1max, bT)_2$ $1pT_{kt} := \ln(pT_{kt})$ $mt := slope(TpT, 1pT)$ $bt := intercept(TpT, 1pT)$ $linT_j := \exp(bt) \cdot \exp(mt \cdot T_j)$

*Steps 1334: Calculate Exponential Fit to Index Finger Force Decay Curve:*

$bI := s1max \cdot 0.30$ $npI := peak(S2b, N, time, s2max, bI)_0 \quad ki := 0..npI$ $pI := peak(S2b, N, time, s2max, bI)_1$ $TpI := peak(S2b, N, time, s2max, bI)_2$ $1pI_{ki} := \ln(pI_{ki})$ $mi := slope(TpI, 1pI)$ $peak(x, N, time, xmax, bb) := $
```
k ← -1
base ← bb
max ← 0
ct ← 0
swt ← 1
for j ∈ 0..N-2
    px_j ← x_j / 1
    if px_j > base
        swt ← 0
        ct ← ct+1
        if x_j > max
            max ← x_j
            T ← time_j
    if px_j < base
        if swt < 1
```
Ⓐ Ⓑ Ⓒ

*FIG. 16-2A*

Step 1328: Determine The Individual Force Pulse Minimums For Each Digit Vector:

$$Pmin(x, NP, timp) := \begin{vmatrix} pmn \leftarrow -10 \\ \text{for } j \in 0..NP-1 \\ \quad \begin{vmatrix} T1 \leftarrow floor(79 \cdot timp_j) \\ T2 \leftarrow floor(79 \cdot timp_j + 1) \\ rng \leftarrow T2 - T1 \\ pmn \leftarrow -10 \\ \text{for } k \in 0..rng-1 \\ \quad \text{if } x_{k+T1} < pmn \\ \quad \quad \begin{vmatrix} pmin_j \leftarrow x_k + T1 \\ tmin_j \leftarrow k + T1 \\ pmn \leftarrow pmin_j \end{vmatrix} \end{vmatrix} \\ \begin{bmatrix} pmin \\ tmin \end{bmatrix} \\ \overline{\begin{bmatrix} 79 \\ NP \end{bmatrix}} \end{vmatrix}$$

For the Thumb:

$mpT := Pmin(S1b, npT, TpT)_0$
$mpT_{npT} := mpT_{npT} - 1$
$mTT := Pmin(S1b, npT, TpT)_1$
$mTT_{npT} := mTT_{npT} - 1$

For the Index Finger:

$mpI := Pmin(S2b, npI, TpI)_0$
$mpI_{npI} := mpI_{npI} - 1$
$mTI := Pmin(S2b, npI, TpI)_1$
$mTI_{npI} := mTI_{npI} - 1$

For the Fifth Digit:

$mp5 := Pmin(S5b, np5, Tp5)_0$
$mp5_{np5} := mp5_{np5} - 1$
$mT5 := Pmin(S5b, np5, Tp5)_1$
$mT5_{np5} := mT5_{np5} - 1$

*FIG. 16-3*

Step 1336, 1338, and 1340: Determine the Pulse Timing Parameters for the Digit Vectors Including the Mean Onset Time and Their Standard Deviations:

Define the sum axis at 50% of the mean applied force:

$axisT := 0.5 \cdot mfT$    $axisI := 0.5 \cdot mfI$    $axisF := 0.5 \cdot mf5$ $$pulse(x, N, time, axis) := \begin{vmatrix} k \leftarrow -10 \\ swt \leftarrow 1 \\ \text{for } j \in 0..N-2 \\ \quad \text{if } x_j > axis \quad \text{if } swt > 0 \\ \quad\quad \begin{vmatrix} On_k \leftarrow time_j \\ swt \leftarrow 0 \end{vmatrix} \\ \quad \text{if } x_j < axis \quad \text{if } swt < 1 \\ \quad\quad \begin{vmatrix} Off_k \leftarrow time_j \\ swt \leftarrow 1 \\ k \leftarrow k+1 \end{vmatrix} \\ \begin{bmatrix} k \\ On \\ Off \end{bmatrix} \end{vmatrix}$$

Thumb Pulse Width and Dead time:

$nT := pulse(S1b, N, time, axisT)_0$ $kj := 0..nT - 1$ $TOn := pulse(S1b, N, time, axisT)_1$ $TOff := pulse(S1b, N, time, axisT)_2$ $Twidth_{kj} := TOff_{kj} - TOn_{kj}$ $kj := 0..nT - 2$ $Tdead_{kj} := TOn_{kj+1} - TOff_{kj}$ $WidthT := mean(Twidth)$    $SDTW := Stdev(Twidth)$
$DeadT := mean(Tdead)$    $SDTD := Stdev(Tdead)$

*FIG. 16-4A*

Index Pulse Width and Dead time:

$nI := pulse(S2b, N, time, axisI)_0$ $kjj := 0 .. nI - 1$ $IOn := pulse(S2b, N, time, axisI)_1$ $IOff := pulse(S2b, N, time, axisI)_2$ $Iwidth_{kjj} := IOff_{kjj} - IOn_{kjj}$ $kjj := 0 .. nI - 2$ $Ideal_{kjj} := IOn_{kjj+1} - IOff_{kjj}$ $WidthI := mean(Iwidth)$  $SDIW := Stdev(Iwidth)$
$DeadI := mean(Ideal)$  $SDID := Stdev(Ideal)$

Fifth Pulse Width and Dead time:

$n5 := pulse(S5b, N, time, axisF)_0$ $kjj := 0 .. n5 - 1$ $FOn := pulse(S5b, N, time, axisF)_1$ $FOff := pulse(S5b, N, time, axisF)_2$ $Fwidth_{kjj} := FOff_{kjj} - FOn_{kjj}$ $kjj := 0 .. n5 - 2$ $Fdead_{kjj} := FOn_{kjj+1} - FOff_{kjj}$ $WidthF := mean(Fwidth)$  $SDFW := Stdev(Fwidth)$
$DeadF := mean(Fdead)$  $SDFD := Stdev(Fdead)$

Mean Onset:

$OnSetT := WidthT + DeadT$  $OnSetI := WidthI + DeadI$  $OnSetF := WidthF + DeadF$

*FIG. 16-4B*

Step 1342: Compute Quality Factors:

Step 1344: Compute Quality Factor From Eq. 6

$$Qf := \sqrt{\left[\frac{(mt-mi)}{mt}\right]^2 + \left(\frac{(mt-m5)}{mt}\right)^2 + \left(\frac{(mt-m5)}{mt}\right)^2} \qquad j1 := 1.6$$

$$Qf := 0.6009$$
$$Q_1 := Qf$$

Step 1346: Compute Quality Factor From Eq. 7

$$Qr := \sqrt{\left(\frac{r_1 - r_5}{r_1}\right)^2 + \left(\frac{r_1 - r_{25}}{r_1}\right)^2 + \left(\frac{r_5 - r_{25}}{r_1}\right)^2} \cdot cr \qquad cr := 67$$

$$Qr := 0.6383$$
$$Q_2 := Qr$$

Step 1348: Compute Quality Factor For Pulse Width From Eq. 8 $cpw := 50$ $$Qpw := \sqrt{\left(\frac{WidthT - WidthI}{WidthT}\right)^2 + \left(\frac{WidthT - WidthI}{WidthT}\right)^2 + \left(\frac{WidthI - WidthF}{WidthT}\right)^2} \cdot cpw$$

$$Qpw := 0.7085$$
$$Q_3 := Qpw$$

Step 1350: Compute Quality Factor For Pulse Width From Eq. 9 $cpo := 50$ $$Qpo := \sqrt{\left(\frac{OnSetT - OnSetI}{OnSetT}\right)^2 + \left(\frac{OnSetT - OnSetI}{OnSetT}\right)^2 + \left(\frac{OnSetI - OnSetF}{OnSetT}\right)^2} \cdot cpo$$

$$Qpo := 0.0200$$
$$Q_4 := Qpo$$

FIG. 16-5A

Step 1354: Compute Quality Factor For Maximum Applied Force From Eq. 10 $cpmx := 1$ $jt := 0..npT - 1$
$DifT_{jt} := pT_{jt} - pT_{jt} + 1$
$mDifT := mean(DifT)$ $ji := 0..npI - 1$
$DifI_{ji} := pI_{jt} - pI_{jt} + 1$
$mDifI := mean(DifI)$ $j5 := 0..np5 - 1$
$DifF_{j5} := p5_{j5} - p5_{j5} + 1$
$mDifF := mean(DifF)$ $$Qpmx := \sqrt{\left(\frac{mDifT - mDifI}{mDifT}\right)^2 + \left(\frac{mDifI - mDifF}{mDifT}\right)^2} \cdot cpmx$$

$Qpmx := 0.8060$
$Q_5 := Qpmx$

Step 1352: Compute Quality Factor For Minimum Applied Force From Eq. 11 $cpmn := 1$ $jt := 0..npT - 1$
$DifT_{jt} := mpT_{jt} - mpT_{jt} + 1$
$mDifT := mean(DifT)$ $ji := 0..npI - 1$
$DifI_{ji} := mpI_{ji} - mpI_{ji} + 1$
$mDifI := mean(DifI)$ $j5 := 0..np5 - 1$
$DifF_{j5} := mp5_{j5} - mp5_{j5} + 1$
$mDifF := mean(DifF)$ $$Qpmn := \sqrt{\left(\frac{mDifT - mDifI}{mDifT}\right)^2 + \left(\frac{mDifI - mDifF}{mDifT}\right)^2} \cdot cpmx$$

$Qpmn := 0.6020$
$Q_6 := Qpmn$

*FIG. 16-5B*

Step 1356: Display Desired Results:

Step 1358: Display Time Dependent Force Plots

Step 1360: Display Permuted Pair Cross Plots

Step 1356: Display Desired Results:

Step 1358: Display Time Dependent Force Plots (Continued)

Step 1360: Display Permuted Pair Cross Plots (Continued)

Step 1356: Display Desired Results:

Step 1358: Display Time
Dependent Force Plots
(Continued)

Step 1360: Display Permuted
Pair Cross Plots
(Continued)

Step 1356: Display Desired Results:

Step 1358: Display Time
Dependent Force Plots
(Continued)

Step 1360: Display Permuted
Pair Cross Plots
(Continued)

1364: Summary and Data Storage

Data Summary Sheet:    CheckSum = "Valid"    Date = "Some Date"    Ver = "Version 1.51"
                                CorrChk = "Valid"

Test Subject:    Name = "Patient Name"    Data Collected:    Test Series No.: Test = "S1-1"
Hand Tested:    Hand = "Right"
System Calibrated:    Calibrated = "Last Calibration Date"

Quality Index:

| $Q_{j1}$ |
|---|
| 0.6009 |
| 0.6383 |
| 0.7085 |
| 0.0200 |
| 0.8060 |
| 0.6020 |

Fatigue Q
Correlation Q
Pulse Width
Pulse Onset
Pulse Maximum
Pulse Minimum

Cross Plot Slopes:
   Sum Versus Thumb:    $SL_{sum} = 0.9711$
   Index Versus Thumb:    $SL_1 = 0.7423$
   Fifth Versus Thumb:    $SL_5 = 0.3790$
   Index Versus Fifth:    $SL_{25} = 1.9333$ Cross Plot Pearson Correlations (r):
   Sum Versus Thumb:    $r_{sum} = 0.9997$
   Index Versus Thumb:    $r_1 = 0.9994$
   Fifth Versus Thumb:    $r_5 = 0.9949$
   Index Versus Fifth:    $r_{25} = 0.9916$ Decay of Applied Force (Fatigue) (kgf/sec):
   Thumb:    $mt = -0.0039$
   Index:    $mi = -0.0030$
   Fifth:    $m5 = -0.0049$

FIG. 16-9A

Initial Maximum Applied Force (kgf):
   Thumb:    i3T = 5.6943
   Index:    i3I = 4.1813
   Fifth:    i35 = 2.3092

Mean Applied Force (kgf) & SD:
   Thumb:    mfT = 4.8866 +/- mfTsd = 0.4102
   Index:    mfI = 3.6324 +/- mfIsd = 0.2805
   Fifth:    mf5 = 1.9452 +/- mf5sd = 0.1904

Mean pulse width and SD (s):
   Thumb:    WidthT = 1.1208 +/- SDTW = 0.0524
   Index:    WidthI = 1.1203 +/- SDIW = 0.0531
   Fifth:    WidthF = 1.1318 +/- SDFW = 0.0513

Mean time between pulses & SD (s):
   DeadT = 1.2544 +/- SDTD = 0.0475
   DeadI = 1.2550 +/- SDID = 0.0486
   DeadF = 1.2441 +/- SDFD = 0.0476

SYSTEM AND METHOD FOR PROVIDING QUANTIFIED AND QUALITATIVE HAND ANALYSIS

BACKGROUND

1. Field of the Invention

The present invention relates to non-invasive devices and methods for measuring and evaluating the absolute and relative muscular strength and the relative coordination of hand digits innervated by the median and ulnar nerves to detect the presence, type and severity of disease. Specifically, the present invention provides a method and apparatus by which the ratiometric strengths and the coordination of the digits may be measured and analyzed to distinguish between repetitive motion injuries such as Carpal Tunnel Syndrome (CTS) and other neural or trauma induced injuries or diseases affecting the hand.

2. Description of the Background

Repetitive motion disorders such as carpal tunnel syndrome are the most common occupational illnesses being reported among a wide range of professions which involve significant hand/wrist motions such as typists (particularly forceful typists) and meat cutters, etc. Carpal tunnel syndrome (CTS) symptoms include: decreased strength; paresthesias (burning or tingling) in the thumb and adjacent fingers; pain in the wrist, palm, forearm; decreased median nerve conduction velocities; and sensory loss in areas of the hand innervated by the median nerve.

Symptoms resembling CTS maybe due to chronic diseases such as rheumatoid arthritis or diabetes mellitus, congenital defects, acute trauma, age, birth control pill usage, and pregnancy. Historically, to aid in the diagnosis of the symptoms, Tinel's Sign, Phalen's Test, and electromyography nerve conduction tests are usually conducted. Additional tests have been developed to aid in symptom diagnosis which are based on specific measurable parameters such as: the expected weakness of the diseased hand; the decreased sensitivity of the fingers to applied vibrational stimulus; restricted range of motion; sensitivity to applied pressure; and chemical analysis of body proteins.

By lightly percussing the course of the median nerve for several seconds, a tingling sensation may be felt in the distribution of the median nerve, indicating a positive Tinel's Sign that suggests that CTS may be present. Phalen's Test generally requires the patient to press the backs of both hands together forming right angles, or holding the patient's wrist in acute flexion for 60 seconds. Numbness or tingling developing over the distribution of the median nerve is an indication that CTS is possible. Positive results in these tests are usually followed by electromyography (EMG) nerve conduction studies. An EMG is sensitive enough to detect the syndrome in 85% of those tested. However, a positive test result cannot be achieved in cases where the nerve has not been damaged to the extent that conduction has been impaired.

Presently, objective clinical information regarding the structure and functionality of the nervous system may be collected by recording electrical signals generated or propagated through the muscular or neural paths of interest. These electrodiagnostic tests require electrodes to be affixed to the patient under study so that electrical signals passing through the area of study may be collected and recorded. In general, these systems require the use of electrodes for both collection and stimulation, which may cause surface burns and/or pain to the patient during the evaluation. Two safety issues are present when using these tests: patient/practitioner contamination due to blood borne infection, and possible electrical shock. Both of these hazards may be minimized through disposable electrodes and through proper electrical shielding to make the systems "touch-proof" (shock-proof).

A number of devices, not relying on the art of electrodiagnostics, have been used to measure a variety of parameters which are intended to provide evidence of injury, specifically CTS. These devices fall into distinct categories which rely on different physical concepts or address specific symptoms. These groups are:

Muscle Strength: Device measures the strength of the finger(s), thumb, or the whole hand grip.

Vibration Threshold: Device measures the threshold of the finger's sensitivity to applied vibrations.

External Pressure: Device applies an external pressure to the appropriate nerve pathway and then asks for subjective report of numbness or weakness.

Body Mobility: Device assesses range of motion in conjunction with EMG testing.

Chemical Analysis: Body fluids are extracted and analyzed via electrophoresis or immunoassay to measure relative amounts of proteins which may be used to infer injury.

For example, U.S. Pat. No. 4,774,966 relates to muscle strength measurement. This device is used to measure weakness present in the hand. If present, this weakness might be related to carpal tunnel syndrome and, as such, provide an early identification of the problem. The measurement is accomplished by measuring the strength of the intrinsic hand muscles innervated by the median nerve after it passes through the carpal tunnel. The motion of the hand is limited by the fixture provided such that only the muscles supplied by the median nerve are measured. The test allows screening by comparing the strength measured to a predefined normal strength. If the test individual should indicate weakness, further evaluation would be indicated. Weakness could be due to peripheral neuropathy, cerebral damage, cervical cord damage and neuromuscular disease.

U.S. Pat. No. 5,163,443 relates to muscle strength measurement. The applied forces exerted by the hand, wrist and forearm are measured with the intention of detecting the presence of cumulative trauma disorders, such as CTS. The forces measured are correlated with forces expected or required in specific work tasks, by comparing maximal strength as well as mobility of the limb in question. In addition, the system allows for grip and finger strength measurement. These measurements are made by a single transducer.

U.S. Pat. No. 5,471,996 relates to muscle strength measurement. The apparatus allows measurement of the muscle strength of the thumb to be studied. Assessment of the strength of the abductor pollicis brevis is important in the diagnosis of some types of neck and elbow injuries, and for CTS and other hand disorders. This apparatus restrains the hand and allows restricted movement to guarantee a reproducible force is applied by the thumb. Isometric and isokinetic testing is possible with this apparatus.

U.S. Pat. No. 5,002,065 relates to a vibration threshold measurement. Nerve injury may be induced by exposure to excessive vibration, causing the sensory threshold to be increased for the afflicted fingers. It has also been suggested that an increase in the perception threshold for vibration stimuli is the earliest detectable objective sign in patients with CTS. The patient's threshold to vibrational stimuli is measured and used to diagnose and screen for sensory disturbances due to conditions such as CTS. A normalized vibrational stimulus is applied to a finger of the patient. The frequency and amplitude of the stimulus are discrete and variable. As the test ensues and the frequency/amplitude are increased, the patient is requested to indicate the onset of sensory perception of the stimuli. The patient is also asked to indicate the loss of detection of the stimuli while the frequency/amplitude sweep is decreasing. Hand position, temperature, and uniform pressure are addressed during testing.

U.S. Pat. No. 5,230,345 relates to a vibration threshold measurement. CTS in a patient is detected by utilizing a vibratory waveform having a discrete frequency and a variable amplitude. The waveform is applied directly to the finger via contact with a speaker cone. A single finger is measured during the test procedure. When the stimuli is detected by the patient, the patient "clicks" the mouse which sends a control signal to the computer. This procedure is completed three times and the results averaged. The results are compared to a predetermined threshold baseline. Measurements exceeding the baseline indicate a diseased condition in the patient.

U.S. Pat. No. 5,301,683 relates to an external pressure measurement. Direct pressure applied for thirty seconds to the median nerve as it passes through the carpal tunnel at the base of the wrist. Patients having anatomic evidence of CTS will experience and report nu ness, pain, weakness oparesthesias in the distribution of the median nerve distal to the carpel tunnel. The applied pressure is controlled, so that repeatable tests may be accomplished.

U.S. Pat. No. 5,513,651 relates to a body mobility measurement combined with a surface electromyography test. A range of motion arm (ROMA) having six degrees of freedom is utilized to determine the range of motion in the upper and lower back while recording an exerting force on a strain gauge to simulate lifting conditions. This system allows a non-invasive, non-loading test for analyzing myofacial injuries and repetitive stress injuries. A protocol for evaluating the relationship between muscle groups is provided to determine if the problem is cervical, CTS or cubital tunnel.

U.S. Pat. No. 5,583,201 relates to a chemical analysis measurement useful for the diagnosis of peripheral nerve damage, including the damage which causes back and neck pain. A body fluid sample is extracted and subjected to a two-dimensional electrophoresis or an immunoassay. A diagnosis can be made by comparing the relative amounts of protein or proteins which increase or decrease in concentration to a standard control. This study determines whether the pain is caused by muscle or fibrous tissue injury.

The measurements described above relating to the strength of the muscles under study use predetermined standards of what is considered normal. The measurements are also limited to the muscle groups innervated by the median nerve. Since the hand also involves the ulnar nerve (fourth digit or ring finger and fifth digit or little finger), these measurements are not conclusive. Individual strength variations due to relative degree of muscle tone could also affect the results of these studies. The measurements relating to vibration sensitivity rely on the patient's compliance to provide an accurate threshold determination. The external pressure measurement described also relies on patient response. The mobility measurements described use EMG measurements in conjunction with the range of motion tests to remove the patient's subjective involvement. The chemical assay methodology described does not require the patient's compliance, but is invasive.

SUMMARY OF THE INVENTION

The invention overcomes the problems and disadvantages associated with current strategies and designs and provides new devices and methods for the non-invasive measurement and evaluation of the absolute and relative muscular strength and the relative coordination of hand digits innervated by the median and ulnar nerves to detect the presence, type and severity of disease.

One embodiment of the invention is directed to a method for qualitatively evaluating the digital performance of a person comprising the steps of measuring a first applied force as a function of time, the force being applied by the first digit of the hand (thumb) to a first force detector, to determine a first data set, measuring a second applied force as a function of time, the force being applied by a digit innervated by the median nerve to a second force detector, to determine a second data set, measuring a third applied force as a function of time, the force being applied by a digit innervated by the ulnar nerve to a third force detector, to determine a third data set, and cross-correlating the first, second and third data sets to create a patient digital performance profile. The patient's digital performance profile may then be compared to a plurality of predetermined diagnostic digital profiles, each of which corresponds to a particular or different disease, in order to assess the physical status of the patient.

Another embodiment of the invention is directed to a method for qualitatively evaluating the digital performance of a person to detect disease comprising the steps of measuring a first applied force as a function of time, the force being applied by a thumb to a first force detector, to determine a first data set, measuring a second applied force as a function of time, the force being applied by a digit innervated by the median nerve to a second force detector, to determine a second data set, measuring a third applied force as a function of time, the force being applied by a digit innervated by the ulnar nerve to a third force detector, to determine a third data set, and substituting or incorporating all or a portion of the first, second and third data sets into one or more quality index formulas to determine one or more patient quality indices, comparing the one or more patient quality indices to a plurality of predetermined diagnostic quality indices, each of which corresponds to a different disease, and detecting the presence of disease.

Another embodiment of the invention is directed to a method for evaluating the digital performance of a person to detect disease comprising the steps of evaluating the relative strength, relative coordination and relative fatigue rates of a digit innervated by the median nerve and a digit innervated by the ulnar nerve to obtain a patient performance data set, and comparing the patient performance data set to a plurality of data sets characteristic of the digital performance of normal individuals and individuals suffering from different diseases, to determine the disease status of the person. The disease status may be the presence or absence of a detectable disease, such as carpal tunnel syndrome, multiple sclerosis, Parkinson's disease, ALS, polio, thoracic outlet syndrome and any other disease which may affect the hand.

Another embodiment of the invention is directed to a diagnostic profile library for diagnosing the presence or absence of disease in a patient based on the digital performance of the patient. The library comprises a plurality of diagnostic digital performance profiles, each of the diagnostic digital performance profiles correlating with the presence of a different disease, the diagnostic digital performance profiles determined by evaluating performance of a median nerve innervated digit and an ulnar nerve innervated digit for each of a plurality of persons having been diagnosed with the disease, and determining the characteristics of the diagnostic performance profile correlatable with the disease.

Another embodiment of the invention is directed to a data base comprising a plurality of data sets as measured from a plurality of patients, the data sets each comprising measurements of the relative strength, relative coordination and relative fatigue rates of a digit innervated by the median nerve and a digit innervated by the ulnar nerve for each of the plurality of patients. The data sets may be categorized based on disease status or the presence or absence of mechanical or other injury. Data sets are preferably cross-correlated for an identified physical condition.

Still another embodiment is directed to an apparatus for evaluating the digital performance of a person's hand to detect disease comprising a plurality of digit contact members for engagement with the digits of the hand and a plurality of force detector means. The plurality of digit contact members comprises a thumb contact member engageable by the thumb of the hand and a lateral digit contact member engageable by a lateral digit of the hand. As used herein, a "lateral digit" is a digit innervated in whole or in part by the ulnar nerve. The plurality of force detector means includes a first force detector means operatively connected to the lateral digit contact member and a second force detector means operatively connected to a digit contact member engaged by a medial digit. As used herein, a "medial digit" is a digit which is innervated in whole or in part by the median nerve. Each of the force detector means is adapted to measure the quantity of force applied to the respective contact member and produces an output indicative of the quantity of force. Preferably, the first and second force detector means further comprise means for measuring force as a function of time. The apparatus may further comprise means for displaying the outputs.

Other objects and advantages of the invention are set forth in part in the description which follows, and in part, will be obvious from this description, or may be learned from the practice of the invention.

DESCRIPTION OF THE DRAWINGS

FIG. 2 is a force diagram showing the determination of the critical angles of forces applied with the fixture of FIG. 1 and determined as in FIG. 1a.

FIG. 4b is a comparative plot of force versus elapsed time measurements for the fifth digit of a person utilizing the same system as with FIG. 4a.

FIG. 14 is an example of a data array for part of a single pulse.

FIG. 15 is a sample data set from a MathCad data sheet.

DESCRIPTION OF THE INVENTION

Figure 1:
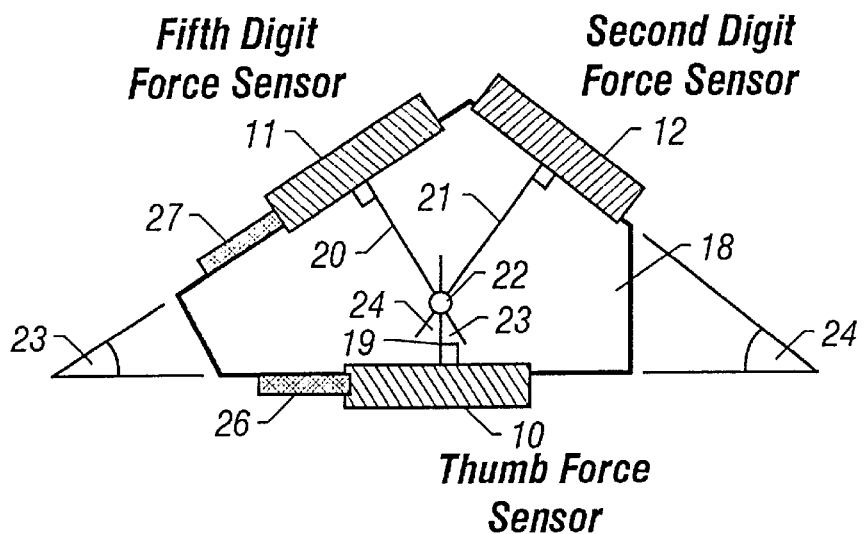
FIG. 1 is a schematic representation of an adjustable fixture which supports the force detectors used in the non-invasive system and method of the present invention according to a preferred embodiment thereof.

As embodied and broadly described herein, the present invention is directed to a method and apparatus by which the ratiometric strengths and the coordination of the digits may be measured and analyzed to distinguish between repetitive motion injuries such as Carpal Tunnel Syndrome (CTS) and other neural or trauma induced injuries or diseases affecting the hand. The present invention also relates to a method for using the apparatus of the invention to calculate quality factors or indices which may be used to provide rapid and repeatable assessment of the tested hand(s).

Specifically, the present invention provides a system for measuring and methods for analyzing the measured force applied by digits of the hand as a function of time and as a function of the hand-wrist position (e.g., flexed or neutral). This invention provides a method which determines the muscle fatigue rates and the relative coordination exhibited by the digits under study. The muscle fatigue rates and the relative coordination exhibited by the digits under study may be used to compute quality factors or indices which may be used to infer the condition(s) of the patient, including the patient's hand(s), under study. Useful quality factors according to the present invention may be computed using the applied force decay coefficients, Pearson's linear correlation coefficients, and other measured and calculated parameters which may be determined by the hand sensor.

The applied forces are measured using suitable force detectors such as strain gauges which may be accurately calibrated to provide long term trend studies of the subject hand(s). These detectors are placed onto a fixture which is held by the subject, allowing the subject hand to open and close in a manner "normal" for that hand. The subject is asked to perform a series of fingertip squeeze motions which could range from a single squeeze held as long as the subject is capable to a series of squeeze, release, squeeze, release patterns which may last from a few seconds to several minutes. The time dependent forces exerted by the subject are recorded and stored for analysis.

For the most effective analysis of the hand, the thumb and at least two other fingers are involved in a test. As used herein, the "first digit" or "digit 1" refers to the thumb, the "second digit" or "digit 2" refers to the index finger, the "third digit" or "digit 3" refers to the middle finger, the "fourth digit" or "digit 4" refers to the ring finger, and the "fifth digit" or "digit 5" refers to the little finger. Measurements are made from at least two digits, one of which is innervated by the median nerve (first, second, third and fourth digits) and one of which is innervated by the ulnar nerve (fourth and fifth digits), the fourth digit being innervated by both the median and ulnar nerves.

A preferred embodiment of the invention measures the triad of forces applied by the thumb opposed and necessarily balanced by the index and little fingers (first, second and fifth digits), forming a triangular force system. The thumb balances the forces exerted by the two fingers. How this balance is accomplished by the subject provides information concerning the health of the muscles and nerves involved in the measurement. By forming a triangle as described, problems residing in the median nerve but not in the ulnar nerve (or vice versa), or in both nerve paths, are clearly delineated. The presence or absence of pain will also affect the way in which these forces are balanced. Cross plots of all possible pairs of the measured forces provide diagnostics which may also infer hand coordination. Although generally speeds of 100 ms are adequate to measure reactions, the present invention is able to resolve data sample times in shorter increments such as, for example, 13 ms down to as little as 1 ms or less. Poor coordination between any two of the measured digits is demonstrated by very erratic (jerky) cross plots produced by jerky hand motions. The muscle fatigue may be determined from these data by computing the rate of decay or force attenuation as a function of the time that the forces are applied. All of these parameters, applied force, coordination, fatigue, etc., may be determined as a function of minutes, hours, days, weeks, or even years. In this manner, documentation is provided concerning the relative and absolute health of the subject's hand(s).

These measurements may be made using different hand-wrist configuration so that differences observed in the subject's hand response may be correlated to position as desired. This would be useful in the cases where nerve damage detectable by electrodiagnostic methods has not yet occurred but pain is reported by the subject. Differences in the subject's test results with the hand-wrist in the neutral position verses a flexed position would help quantify the diagnosis.

In other embodiments, springs, air bags, or other like instruments may be placed on or under the force detectors of the hand fixture to allow a measurement of both the applied force and the displacement caused by the force. The displacement would be useful in studying or in determining types of motion responsible for any detected injury.

One embodiment of the present invention uses the time dependent data collected by the hand sensor to form the basis of quality indices. These indices exacerbate differences, especially sign differences, which may exist in the test data used to calculate the quality indices. This is accomplished by forming a quadrature sum of paired data differences. By making the differences between the normal and injured digits large, developing neurological problems appear distinct from the normal responses. By computing several quality factors or quality indices, the probability of an incorrect analysis decreases. In addition, the combinations of the quality factors or quality indices aid in the analysis of the type of injury present in the hand being evaluated, increasing the sensitivity of the diagnosis.

Thus, the present invention provides rapid, non-invasive, reproducible, quantifiable measurements of the following:

Measurement of relative and absolute digit strength for the hand(s) under study, which may be compared to tests completed months or years earlier in a statistically significant manner.

Measurement of muscle fatigue rates so that long term studies will be able to discern improvement or degradation of the hand(s).

Measurement of relative hand coordination which will provide quantified documentation for improvement or degradation of the hand(s).

Measurements which will clearly support or defeat claims of muscle or nerve damage related to repetitive motion injury, carpal tunnel injury, trauma, or other neural disorder.

Measurements useful in the diagnosis of type and progression of disease.

A schematic representation of a force sensor fixture according to a preferred embodiment is shown in FIG. 1. This fixture 18 may be made from a solid block of material or, more preferably, is made to be adjustable to accommodate more than one individual subject. An important feature of the latter embodiment of this fixture is the ability to adjust the placement of the force sensors or detectors, 10, 11 and 12, such that their alignment is perpendicular to the "normal" gripping motion of the test subject's hand or fingers. These detectors are aligned by the adjustments represented at 26 and 27 such that the force projections 19, 20, and 21 meet at a point 22. This geometry minimizes side loading of the sensors out of the plane of the fixture and ensures that the stability of the fixture 18 may be easily controlled by the test subject. This configuration also allows any side loading present in the plane of the fixture due to poor hand coordination to be trigonometrically resolved.

Figure 1A:
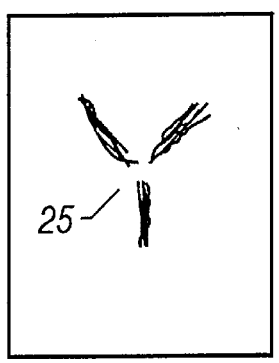
FIG. 1a is a marking on paper by a test subject to determine critical angles of motion between digits thereof.
Figure 2:
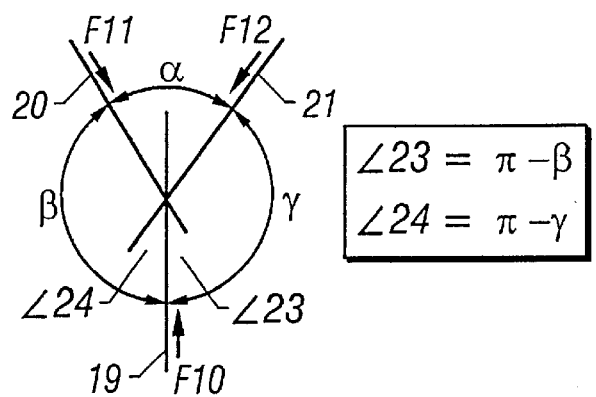

A solid block has the advantage of being very rigid, reducing elastic compression of the fixture during compression of the force sensors. An adjustable fixture has the advantage of being useful for more than one individual. The critical angles, 23 and 24, may be determined by noting the "normal" motion of the test subject's digits via a method similar to the following. To determine the "normal" motion, pencils, pens, or chalk, etc. are attached to the test digits of interest, e.g., the first, second and fifth digits, and the test subject is asked to repeatedly scratch on a piece of paper, forming a pattern similar to that shown at 25 in FIG. 1a. By averaging the marks shown in 25, the angles 23 and 24 may be determined by trigonometric means as shown in FIG. 2. After adjusting the angles 23 and 24, the force detectors are adjusted by adjustment mechanisms 26 and 27 to ensure that the perpendicular projections 19, 20 and 21 meet at point 22. Similarly, the angles 23 and 24 may be determined electronically by holding a device which can infer the angles subtended during the gripping motion.

In a preferred embodiment, adjustment mechanisms 26 and 27 comprise screwable caps which allow adjustment of the hand span without recalibrating the load cells.

The fixture is lightly held by the test subject by placing the fingertips of the test digits on the force detectors. This fixture then defines a plane through which the forces must act in order to maintain a grip on the fixture. The fixture is preferably held by the fingertips rather than the finger or thumb joints, as the latter may defeat the balance required for the measurements. The fixture does not limit the hand-wrist orientation, and this orientation may be varied to aid in diagnosis of any suspected illness or injury. This embodiment of the fixture causes the muscle groups innervated by the ulnar and median nerves to work in opposition in order to balance the fixture. Problems present in one or the other, or both nerve systems will be evident in how the digits balance the fixture during tests. Strength of the test subject's hand is not critical since comparative measurements will be made for all three digits. However, due to the fixture geometry, the force exerted by the thumb on the thumb force sensor will always equal the forces exerted by both finger force sensors. This force balance is shown in FIG. 2 and by the equations Eq. (1) and Eq. (2) below. These equalities provide a constant quality check on the sensor calibrations. The angle 23 is given by $\pi-\beta$, and the angle 24 is given by $\pi-\gamma$, expressed in radians.

$$0 = F_{12} \cdot \sin(\pi-\gamma) + F_{11} \cdot \sin(\pi-\beta) \qquad \text{Eq. (1)}$$

$$F_{10} = F_{12} \cdot \cos(\pi-\gamma) + F_{11} \cdot \cos(\pi-\beta) \qquad \text{Eq. (2)}$$

Figure 3:
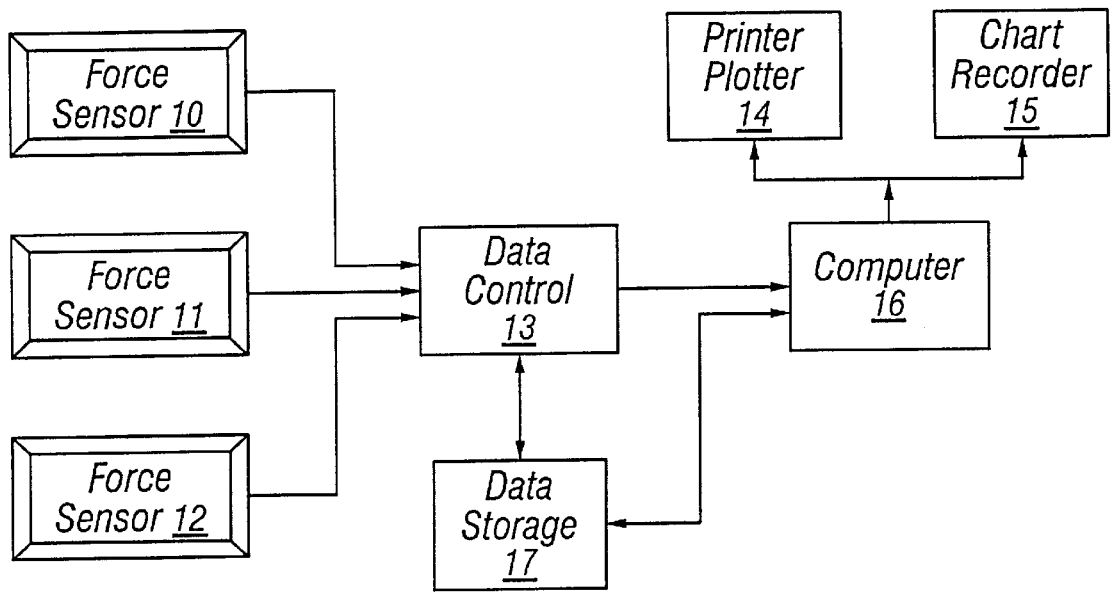
FIG. 3 is a block schematic representing the components used during measurement and display of a preferred embodiment of the invention.

Referring now to FIG. 3, to conduct a test, the subject lightly holds the fixture maintaining the hand-wrist in a prescribed orientation. Fixtures such as bowling or golf braces may be used to help maintain the hand wrist orientation of choice. Upon timing prompts (visual and/or audible) provided by the data control module 13, the test subject squeezes the force sensors, 10, 11, and 12, using only the fingertips. As the test ensues, the data controller 13 collects the data and sends it to storage 17 for later analysis, or to the computer 16 for immediate processing. After processing the data, the results of the test are displayed on the computer 16, printed and/or plotted, 14, 15, and saved to disk 17. The raw data is also available for display on 15 or on the computer 16. Alternately, the data may be directed to a remote location (i.e., a computer web site) for analysis.

Many variations and combinations of regular or irregular squeezes may be studied. For example, short one or two second squeezes may be repeated for several minutes, or longer squeezes held for five or ten seconds may be repeated for several minutes, or a single long pulse of several minutes may be studied. In this manner, hand strength, muscle fatigue, and coordination may be quickly ascertained in a quantifiable, documented manner.

Figure 4A:
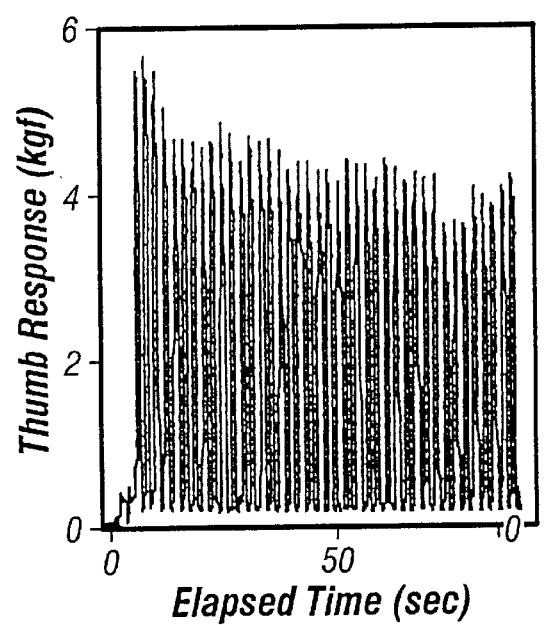
FIG. 4a is a plot of force versus elapsed time measurements for the thumb of a person utilizing the system of the present invention, according to a preferred embodiment thereof.
Figure 4B:
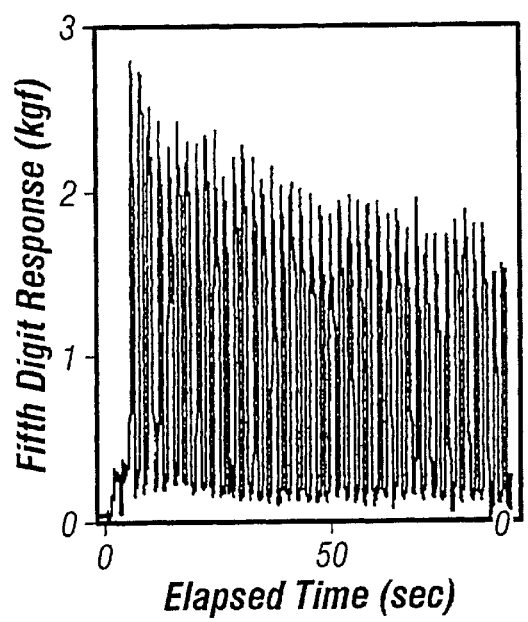
Figure 4C:
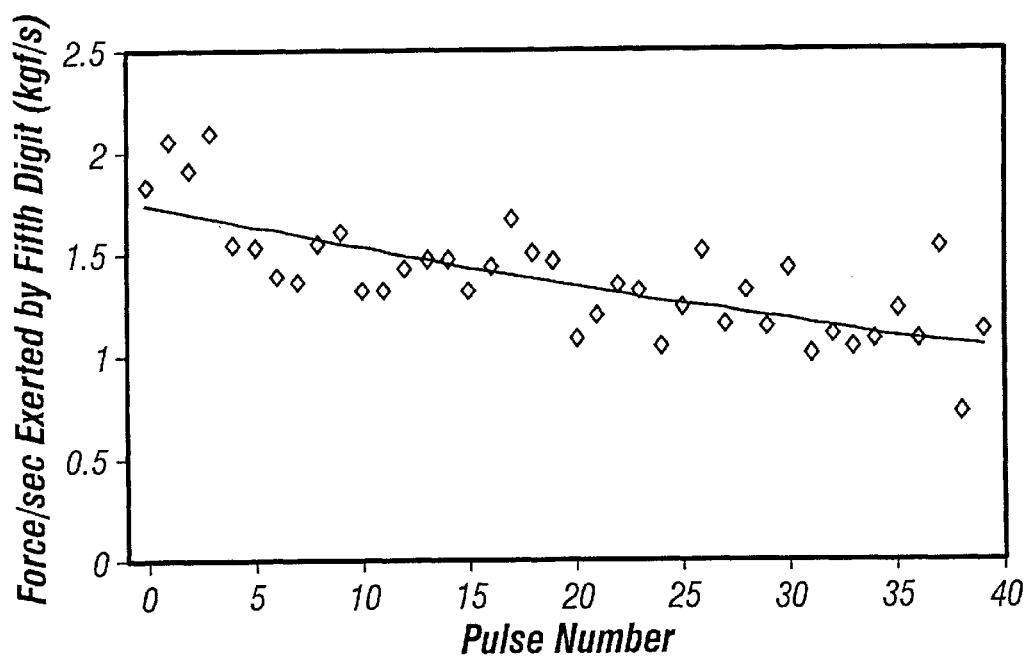
FIG. 4c is a plot of force versus pulse representing muscle fatigue of the fifth digit over a period of time.

Strength and Fatigue:

Referring now to FIGS. 4a, 4b and 4c, applied force data has been collected and displayed for the thumb (FIG. 4a) and the fifth digit (FIG. 4b) as a function of elapsed time. Both plots show a decrease in the applied force (kgf) as a function of elapsed time (sec). If the short term rate of fatigue is defined as $\lambda$, a short term fatigue rate may be computed from the data using Eq. (3):

$$\lambda = \frac{1}{t} \cdot \ln\left(\frac{F}{F_0}\right) \qquad \text{Eq. (3)}$$

where:
t=elapsed time in seconds,
F=force applied by the digit of interest at a time t, and
$F_o$=zero time force intercept, or approximately the initial applied force.

A preferred manner for determining this fatigue rate would be using standard curve fitting techniques, as shown in FIG. 4c, which is a re-plot of the data in FIG. 4b with the pulses integrated and plotted as a function of the pulse number. In this data set, each pulse represents a time step of ~2.3 seconds. In this case the term $F_o$ is the intercept and $\lambda$ would be the slope determined by a least squares exponential fit to the data. Long term fatigue rates may also be determined in a similar manner. Data collected over many minutes, e.g., 15 or 20 minutes, may be used to numerically or graphically determine a long term fatigue rate in like manner. Studies using the present invention have shown that for compliant subjects, the short term fatigue rates collected over 40 seconds are quite similar if not identical to long term fatigue rates collected over 20 minutes. This similarity thereby provides a subject compliance check throughout the tests.

The absolute and ratiometric strengths of the digits involved in the tests may be determined as time averages or as time dependent parameters which may be determined by computing the ratios, ($R_{1T}$, $R_{4T}$, $R_{14}$) of the applied forces as defined by Eq. (4):

$$R_{1T} = \frac{F_1}{F_T}; \quad R_{4T} = \frac{F_4}{F_T}; \quad R_{14} = \frac{F_1}{F_4}; \qquad \text{Eq. (4)}$$

where:
$F_1$=the force applied by the first or index finger (second digit),
$F_4$=the force applied by the fourth or little finger (fifth digit), and
$F_T$=the force applied by the thumb (first digit).

Comparisons made between the digits of interest as a function of time can also provide the absolute muscle strength tests as with dynamometers described above but without the need to compare to a predetermined normalized strength data base. Regardless of the strength of the individual, the ratiometric ratios and the fatigue measurements provide documentation on a specific subject, independent of prior training or abilities. In addition, a non-compliant subject would have to repeat the ratiometric strength results with the appropriate fatigue rates to provide convincing proof of an injury or illness.

Figure 5A:
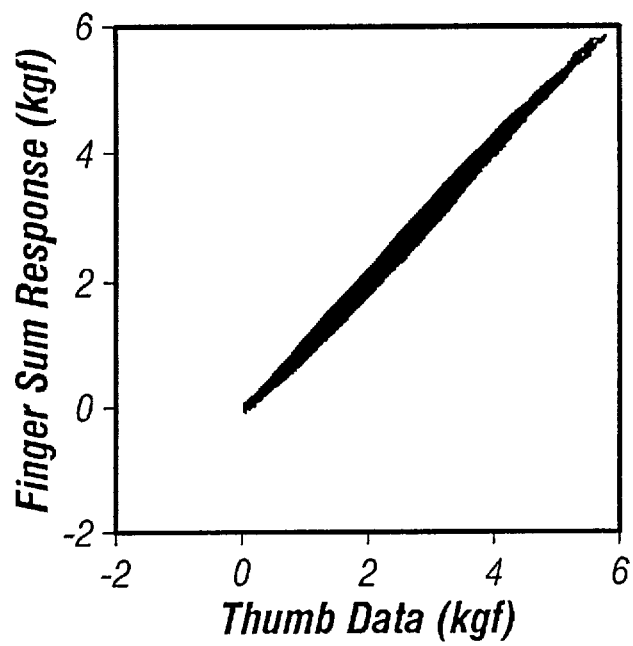
FIGS. 5a–5d show a sequence of plots showing the ratiometric strengths and coordination abilities of the test subject, FIG. 5a representing a quality check by comparing the sum of the finger forces to the opposing thumb force, FIG. 5b representing the data collected for the second and fifth digits, FIG. 5c representing the data collected for the second digit (index finger) and the thumb and FIG. 5d representing the data collected for the fifth digit (little finger) and the thumb.

Coordination:

Referring now to FIGS. 5a through 5d, comparisons may be made between the applied forces exerted by the first, second and fifth digits (thumb, index and little fingers). The force applied by each digit is plotted with respect to a different digit. FIG. 5a shows a quality data check plot. In this plot, the sum of the forces applied by the second and fifth digits (index and little fingers) is plotted against the force applied by the thumb. The Pearson's correlation coefficient for these data is r=0.9996 for the 7132 data points used in this test, indicating a good quality test was completed.

Figure 5B:
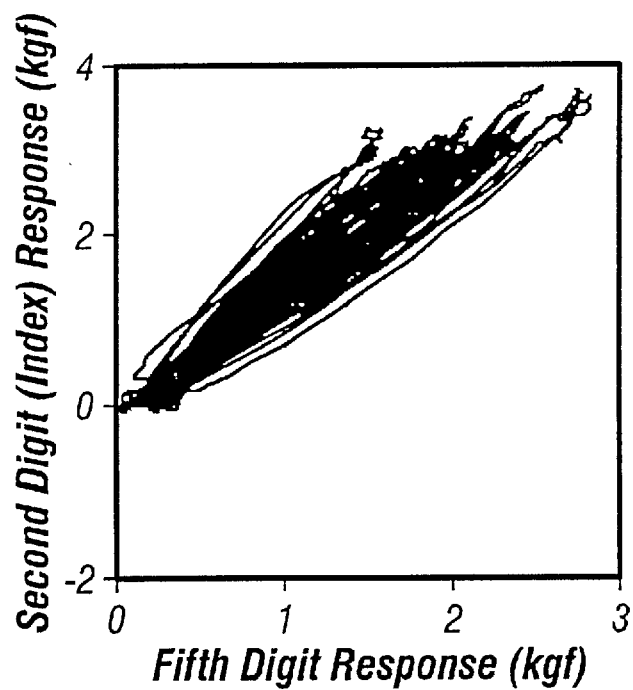
Figure 5C:
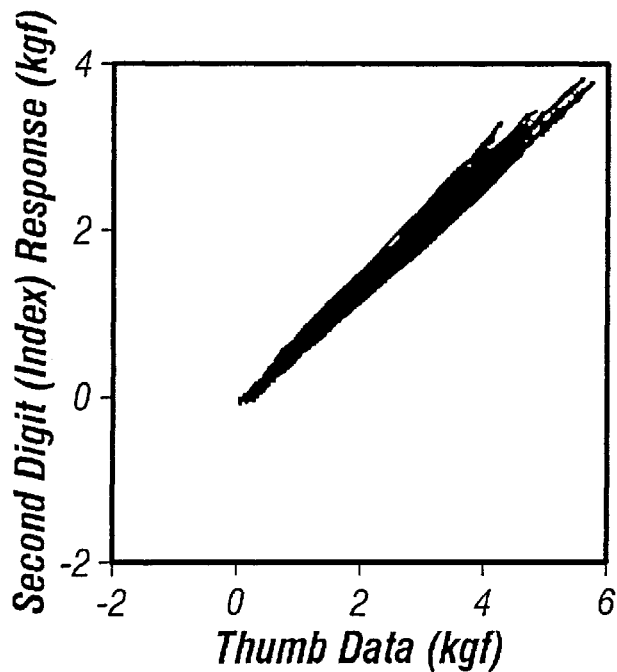
Figure 5D:
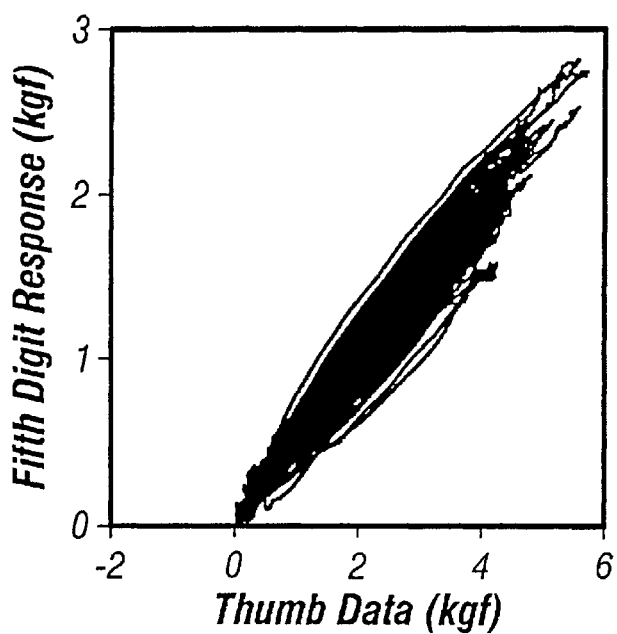

FIG. 5b shows the cross plot of the forces applied by the second digit (median nerve) versus the fifth digit (ulnar nerve). The correlation coefficient is r=0.9820 with n=7132. The cross plot between the thumb and the index finger is shown in FIG. 5c with r=0.9984 and the fifth digit versus thumb data is shown in FIG. 5d where r=0.9904. The data collected in FIGS. 5a through 5d were collected with the hand-wrist in the neutral position from a test subject with no known neural damage to the hand, but trauma injury was known to have occurred in the past due to a sports injury. Note the increased spread in the data collected for the fifth digit when plotted against the thumb and index finger. At the same time, the data between the index finger and thumb is quite narrow. This method of presenting the data allows the practitioner to discriminate between injury to specific digits. These tests may be run using the third or fourth digits (middle and ring fingers) if injury is suspected to those digits. The only requirement is that the proper pair of fingers is chosen to ensure different nerve groups are used in the test. When coupled with hand-wrist positional tests, i.e., neutral versus flexed, a powerful diagnostic screen is provided.

Figure 6A:
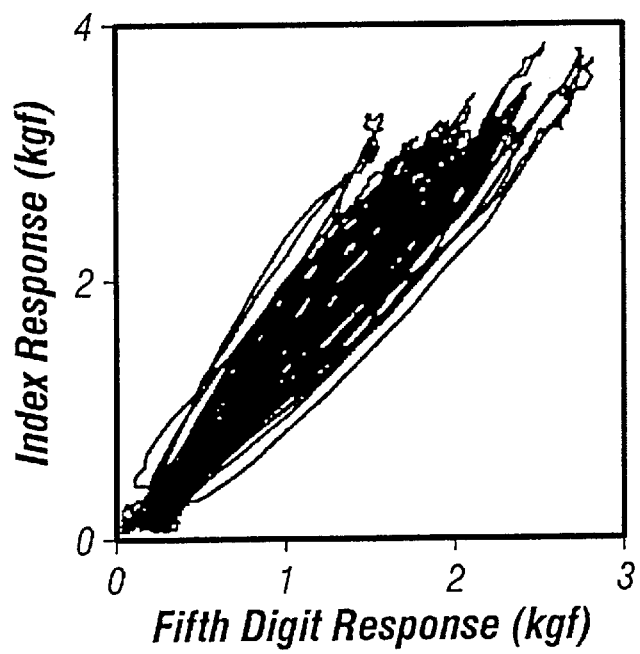
FIGS. 6a–6b are comparison plots of the measured response between the second digit (index finger) and the fifth digit (little finger) for two individuals, FIG. 6a representing applied force and the relatively smooth response of a normal hand, FIG. 6b representing the very erratic behavior in a hand previously diagnosed as suffering from CTS.
Figure 6B:
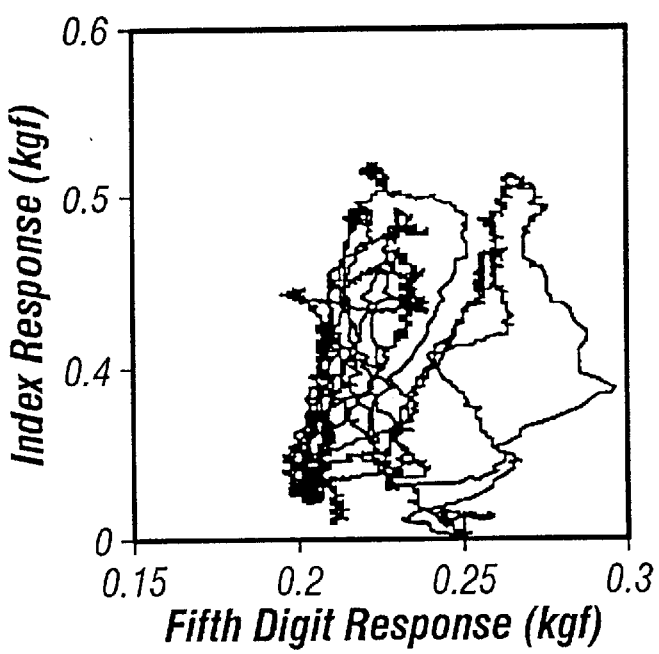

The effectiveness of this screen is shown in FIGS. 6a and 6b. In this case, the data is shown for the second versus the fifth digit (index versus little finger) for the subject in FIG. 5b versus an individual with a known history of CTS. The correlation coefficient for FIG. 6b is r=0.4629, n=5200. Several important points are evident from these cross plots. The subject hand shown in FIG. 6b is weak, very erratic and poorly coordinated. Even without further testing, a problem is evident.

The method presented provides an indication as to the ratiometric strengths of the digits and as to the relative coordination abilities present between the digits of the hand. Compliance should not be an issue during these tests. Attempts by several individuals with no history of CTS to duplicate the results shown in FIG. 6b are unsuccessful. This is due to the natural coordination present in a properly functioning hand. Attempts to "jitter" the data by rapidly changing the applied forces fail because the finger movements are still coordinated on the measurement time scale. Only when the coordination is impaired by poor neural feedback will the data exhibit the erratic behavior shown in FIG. 6b.

The system and methods of the present invention are not limited to application to individuals afflicted with CTS. Any disease or injury affecting the hand may be evaluated by these methods. Since different nerve groups are studied, differential results indicate specific problems characteristic of different diseases. For example, strength and fatigue rates of Multiple Sclerosis patients may be evaluated by these methods, providing documentation as a function of time. In fact, the time and/or frequency related outputs provided by the system of the present invention may be studied and used in diagnosis of specific hand, wrist or arm diseases using pattern recognition, neural networks, frequency analysis, signature analysis, and plotting or graphic displays for visual analysis by trained doctors/medical technicians. The tests described herein may be repeated at hourly, daily, weekly, yearly or other intervals to determine long term effects.

A preferred embodiment and method of the invention utilizes the first, second and fifth digits. Measurements are made from all three, the first and second digit for the median nerve and the fifth digit for the ulnar nerve. Other embodiments of the invention may involve the thumb and any of the other hand digits, or any other three contact points requiring muscle control by muscles innervated by different nerves. However, measurements should be made from at least two digits which involve different nerves, e.g. the median and the ulnar nerves.

In addition, the force sensors or detectors, such as 10, 11 and 12 of FIG. 1, may be adapted with springs, air bags or the like to provide measurements of displacement caused by force exerted by the hand digits. In some cases the fixture might actually include or simulate devices normally used by the tested subject, e.g. a mouse, computer pointing device, computer keyboard, etc. This could lead to redesign or altered use of such devices.

A normally functioning hand can perform most operations in a relatively smooth, repeatable manner. While the strength of the different digits may vary, the relative functionality exhibited between the digits of a normal hand remains smooth and consistent. Just how smoothly and consistently the hand performs these functions can be thought of as coordination. A well-coordinated hand will exhibit similar traits between the five digits of the hand, regardless of the relative strength differences also present between the digits. By considering the relative differences between the digits for a given test and normalizing to the thumb response, it has been discovered that quality indices may be defined and used to detect the presence, type and progression of disease. The quality indices of the present invention should be small (less than 1.0) for a normally functioning hand, but increase to as high as 30 or more based on the presence, type and severity of disease.

By considering the difference between the measurements, important abnormalities such as slope changes are accentuated. In a preferred embodiment, the differences are squared. Squaring the difference removes the sign of the terms and allows the sum to made unambiguously. Taking the square root keeps the results tractable but is not necessary for the quality indices to be valid.

Useful quality indices may be calculated using variations of the following general formula:

$$QI = c \cdot \left( \left( \frac{P_i - P_{i+1}}{P_i} \right)^j + \left( \frac{P_i - P_{i+2}}{P_i} \right)^j + \left( \frac{P_{i+1} - P_{i+2}}{P_i} \right)^j \right)^{\frac{1}{n}} \quad \text{Eq. (5)}$$

where:
QI=the quality index value,
c=multiplier chosen to normalize the quality index,
$p_i$=measured or computed parameter for the first of the tested digits,
$p_{i+1}$=measured or computed parameter for the second of the tested digits,
$p_{i+2}$=measured or computed parameter for the third of the tested digits,
j=2, 4, 6 . . . , and
n=1, 2, 3 . . . .

The parameter $p_i$ may refer to: (1) the thumb; (2) another median nerve innervated digit, such as the index finger; or (3) an ulnar nerve innervated digit, such as the little finger, as desired by the investigator. Whichever is chosen as the first tested digit, the other two digits follow as $p_{i+1}$ and $p_{i+2}$. Preferably, n=2 and c=1.

Some of the specific useful quality indices derived from Eq. (5) are defined below, but quality indices useful in the practice of the invention are not to be limited to those defined in this document. As noted above, the quality indices which follow may optionally be used with multipliers to place the indices on equal scales if desired.

Applied Force Time Dependent Attenuation (Decay) Index; $QI_D$:

$$QI_D = c \cdot \left( \left( \frac{mt - mi}{mt} \right)^2 + \left( \frac{mt - m5}{mt} \right)^2 + \left( \frac{mi - m5}{mt} \right)^2 \right)^{\frac{1}{n}} \quad \text{Eq. (6)}$$

where:
c=the multiplier chosen to normalize the quality index,
mt=the exponential decay slope of the thumb (digit 1),
mi=the exponential decay slope of the index finger (digit 2), m5=the exponential decay slope of the little finger (digit 5), and n=1, 2, 3 . . . .

In a preferred embodiment, c=1 and n=2.

Figure 7:
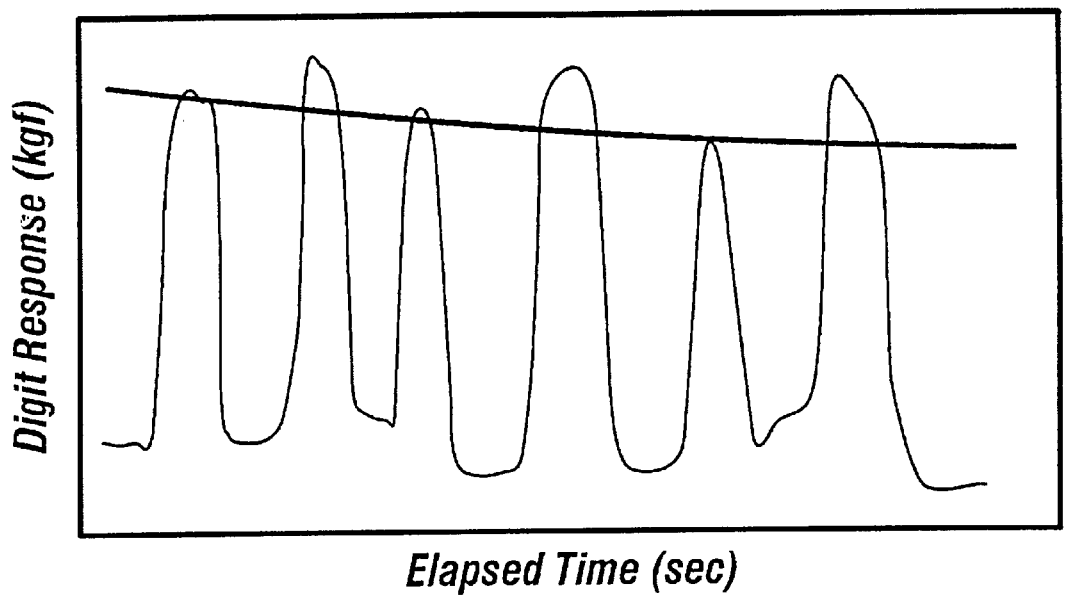
FIG. 7 is a simulated data set showing the exponential decay in applied force exerted by a digit during successive pulses.

This first index is based on the decay or attenuation of applied force by the different digits of the hand. A normal hand exhibits similar force decay constants for each digit used in the test. The simulated data in FIG. 7 represents a data set where the exponential decay or force attenuation has been determined for a single digit during repetitive gripping and releasing. Specifically, FIG. 7 is a schematic representation of the time dependence of the force applied by one of the three digits (thumb, index finger or small finger) during a series squeeze-release-squeeze-release test. The force (y-axis) may be represented by actual force (kgf) (shown) or by a percentage (%) of the maximum force applied during the test. The elapsed time represents the time dependence of the measurement during the test. The curved heavy line drawn through the peaks of the applied force pulses represents the non-linear applied force decay. The slope ($\lambda$) of this force decay will represent a straight line when plotted on a semi-log scale (log force). This slope will be negative for normally decreasing force with respect to time, or positive if the applied force increases with respect to time.

Referring to FIG. 7, the curved heavy line represents this non-linear fit to the applied force and the value of this exponential slope is defined as the exponential decay coefficient e.g., mt, for the first digit or thumb. For "normal" undamaged hands, the QID coefficient will be typically less than one (1.0).

Linear Correlation Coefficient (r); $QI_r$:

$$QI_r = c \cdot \left( \left( \frac{rit - r5t}{rit} \right)^2 + \left( \frac{ri5 - rit}{rit} \right)^2 + \left( \frac{ri5 - r5t}{rit} \right)^2 \right)^{\frac{1}{n}} \quad \text{Eq. (7)}$$

where:

c=the multiplier chosen to normalize the quality index, rit=the Pearson's linear correlation coefficient between the thumb (digit 1) and index finger (digit 2), r5t=the Pearson's linear correlation coefficient between the thumb (digit 1) and little finger (digit 5), ri5=the Pearson's linear correlation coefficient between the index finger (digit 2) and little finger (digit 5), and n=1, 2, 3 . . . .

In a preferred embodiment, c=1 and n=2.

Figure 8:
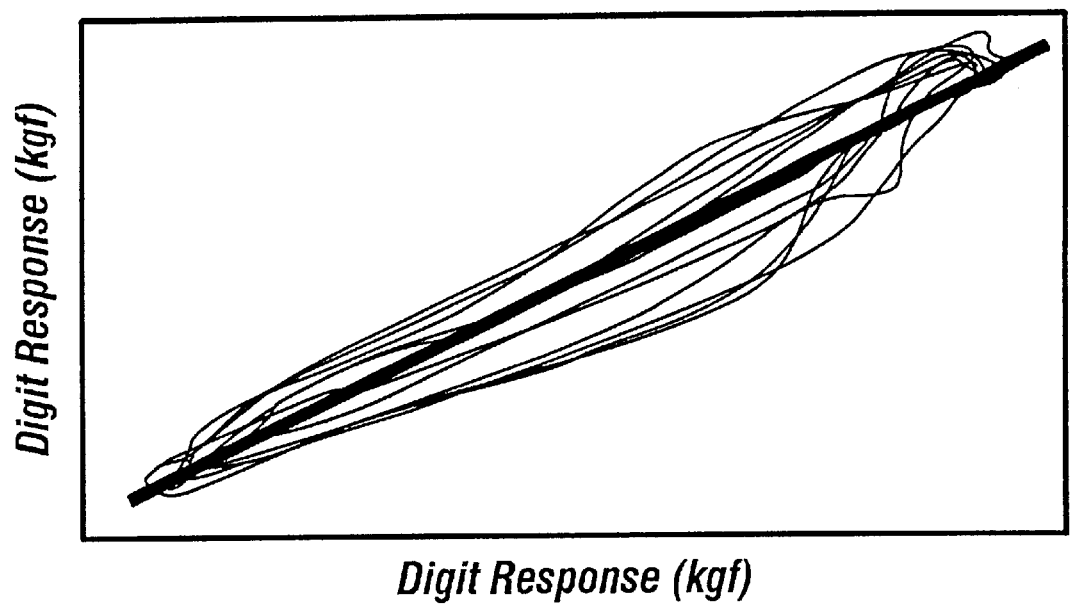
FIG. 8 is a linear slope of a cross plot of the applied forces of two digits.

The heavy solid line in FIG. 8 represents the linear slope of a cross plot between two digits. Specifically, FIG. 8 is a schematic representation of the forces applied by two different digits during a series squeeze-release-squeeze-release test. The two axes represent the applied forces in a cross plot showing the applied force exerted by one digit with respect to the second digit. The straight line drawn through the simulated data represents the Pearson's linear correlation coefficient.

The Pearson's linear correlation is computed for the data set and usually presented as $r^2$ or simply r for the data set. Correlation values near 1.0 indicate that a strong linear correlation exists between the two digits' applied forces. For a "normal" undamaged hand, these correlation values will be quite similar and the overall QI, coefficient will be less than one.

Pulse Width Uncertainty Correlation Coefficient; $QI_{pw}$:

$$QI_{pw} = c \cdot \left( \left( \frac{sdwT - sdwI}{sdwT} \right)^2 + \left( \frac{sdwT - sdw5}{sdwT} \right)^2 + \left( \frac{sdwI - sdw5}{sdwT} \right)^2 \right)^{\frac{1}{n}} \quad \text{Eq. (8)}$$

where:

c=the multiplier chosen to normalize the quality index, sdwT=standard deviation of the full pulse width at half maximum for the thumb (digit 1), sdwI=standard deviation of the full pulse width at half maximum for the index finger (digit 2), sdw5=standard deviation of the full pulse width at half maximum for the little finger (digit 5), and n=1, 2, 3 . . . .

In a preferred embodiment, c=1 and n=2.

Figure 9:
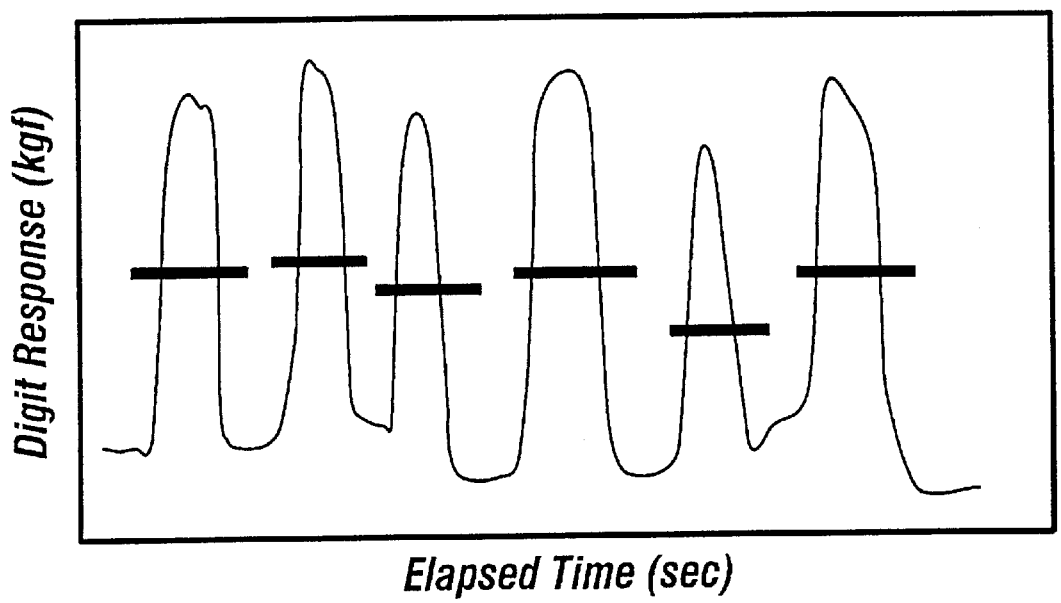
FIG. 9 is a data set showing pulse width during replication by a digit of a uniform pulse train.

This coefficient indicates how well the subject can replicate a uniform pulse train as shown in FIG. 9, where the full width is measured at the pulse half maximum amplitude (fwhm). Specifically, FIG. 9 is a schematic representation of the time dependence of the force applied by one of the three digits during a series squeeze-release-squeeze-release est. The force (y-axis) may be represented by actual force (kgf) (shown) or by a percentage (%) of the maximum force applied during the test. The elapsed time represents the time dependence of the measurement during the test. The bars drawn through the force pulses represent the location for measuring the full width pulse width at half the maximum pulse amplitude or fwhm. This measurement indicates how well a digit can follow the timing pulse for the on-off signal.

Sharply varying values for the pulse onset (rise times) and pulse decay (decay times) will cause large values to be computed for the standard deviation and cause the $QI_{pw}$ efficient to be large. For normal undamaged hands, this coefficient will be less than one. A variation on this coefficient would measure the standard deviation of the pulse width measured at the base or onset time, instead of the fwhm value.

Pulse Onset Correlation coefficient; $QI_{po}$:

$$QI_{po} = c \cdot \left( \left( \frac{OtT - OtI}{OtT} \right)^2 + \left( \frac{OtT - Ot5}{OtT} \right)^2 + \left( \frac{Ot5 - OtI}{OtT} \right)^2 \right)^{\frac{1}{n}} \quad \text{Eq. (9)}$$

where:

c=the multiplier chosen to normalize the quality index,

OtT=standard deviation of the differential pulse onset time for the thumb (digit 1), OtI=standard deviation of the differential pulse onset time for the index finger (digit 2), Ot5=standard deviation of the differential pulse onset time for the little finger (digit 5), and n=1, 2, 3 . . . .

In a preferred embodiment, c=1 and n=2.

Figure 10:
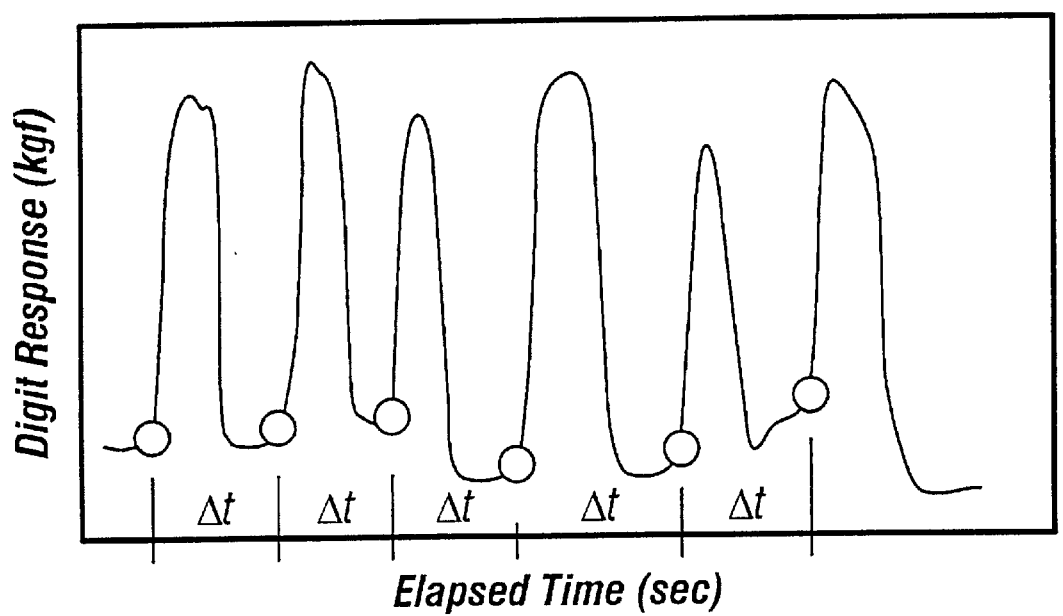
FIG. 10 is a data set showing pulse onset for a digit when the patient repeatedly pulses the apparatus following an audio stimulus.

The simulated data in FIG. 10 indicates how the differential onset time is determined. FIG. 10 is a schematic representation of the time dependence of the force applied by one of the three digits during a series squeeze-release-squeeze-release test. The force (y-axis) may be represented by actual force (kgf) (shown) or by a percentage (%) of the maximum force applied during the test. The elapsed time represents the time dependence of the measurement during the test. The circles drawn at the base of the pulses represent the location for measuring the pulse onset time. The relative difference between successive onset times represents the Δt between the pulses. The time difference between successive pulse onset times forms the basis for this calculation which indicates how uniformly the subject can pulse the apparatus, following an audio stimulus. For uniform pulse trains, the standard deviation will be small, indicating a normal, uninjured hand.

Mean Maximum Applied Force Correlation Coefficient; $QI_{MF}$:

$$QI_{MF} = c \cdot \left( \left( \frac{mfTsd - mfIsd}{mfTsd} \right)^2 + \left( \frac{mfTsd - mf5sd}{mfTsd} \right)^2 + \left( \frac{mf5sd - mfIsd}{mfTsd} \right)^2 \right)^{\frac{1}{n}} \quad \text{Eq. (10)}$$

where:

c=the multiplier chosen to normalize the quality index, mfTsd=standard deviation of the differential maximum applied force by the thumb (digit 1), mfIsd=standard deviation of the differential maximum applied force by the index finger (digit 2), mf5sd=standard deviation of the differential maximum applied force by the little finger (digit 5), and n=1, 2, 3 . . . .

In a preferred embodiment, c=1 and n=2.

Figure 11:
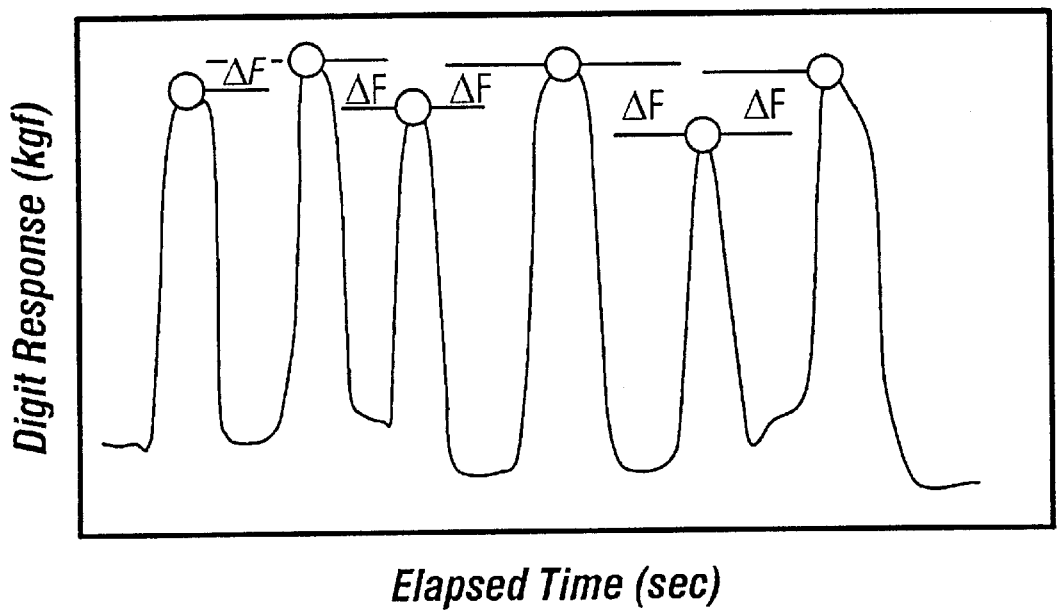
FIG. 11 is a data set depicting the maximum applied force applied by a digit for each successive pulse.

The maximum force exerted by the digits for each pulse is determined as shown in FIG. 11. FIG. 11 is a schematic representation of the time dependence of the force applied by one of the three digits during a series squeeze-release-squeeze-release test. The force (y-axis) may be represented by actual force (kgf) (shown) or by a percentage (%) of the maximum force applied during the test. The elapsed time represents the time dependence of the measurement during the test. The circles drawn at the peaks of the pulses represent the location for measuring the maximum applied force value for each pulse. The relative amplitude difference between successive peak values represents the ΔF between the pulses' peak values. This ΔF value describes the digit's ability to reproduce a smooth pulse profile.

This force typically has an exponential decay associated with the amplitude, and this decay is discussed in Eq. (3) above. By measuring the standard deviation of the differential maximum force, i.e., the difference between successive amplitudes, a measure of the applied force repeatability is obtained. For a normal, uninjured hand, this force differential will be small and relatively uniform even though it will be monotonically decreasing.

Mean Minimum (Resting) Applied Force Correlation Coefficient; $QI_{RF}$:

$$QI_{RF} = c \cdot \left( \left( \frac{mrTsd - mrIsd}{mrTsd} \right)^2 + \left( \frac{mrTsd - mr5sd}{mrTsd} \right)^2 + \left( \frac{mr5sd - mrIsd}{mrTsd} \right)^2 \right)^{\frac{1}{n}} \quad \text{Eq. (11)}$$

where:

c=the multiplier chosen to normalize the quality index, mrTsd=standard deviation of the differential resting applied force for the thumb (digit 1), mrIsd=standard deviation of the differential resting applied force for the index finger (digit 2), mr5sd=standard deviation of the differential resting applied force for the little finger (digit 5), and n=1, 2, 3 . . . .

In a preferred embodiment, c=1 and n=2.

Figure 12:
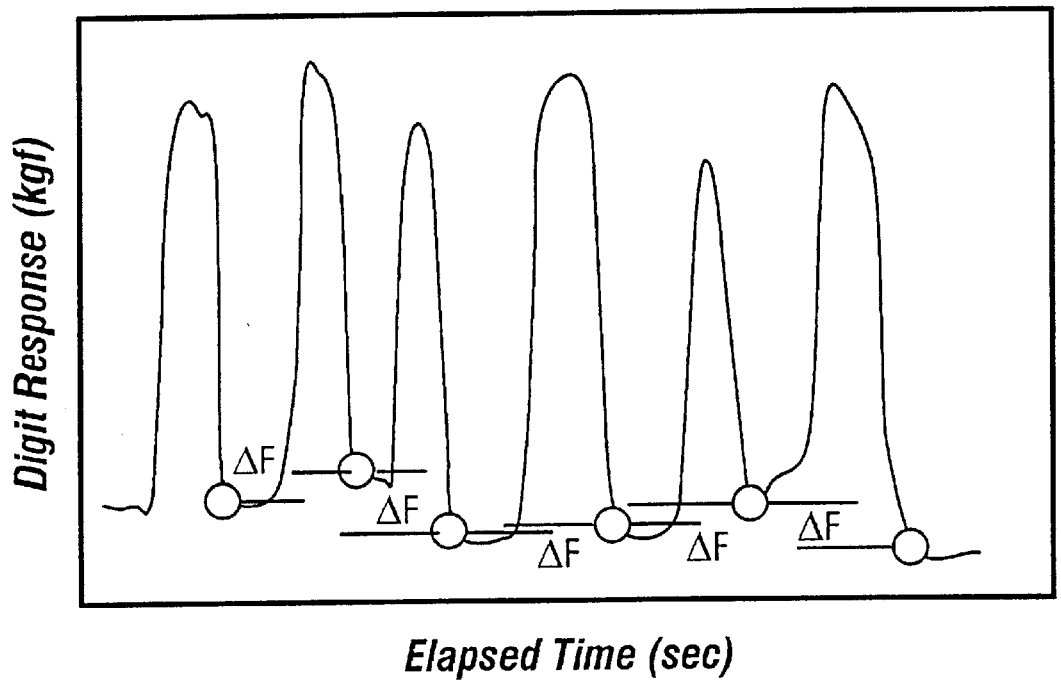
FIG. 12 is a data set showing the minimum or resting force exerted by a digit during successive pulses.

The minimum force exerted by the digits for each pulse is determined as shown in FIG. 12. FIG. 12 is a schematic representation of the time dependence of the force applied by one of the three digits during a series squeeze-release-squeeze-release test. The force (y-axis) may be represented by actual force (kgf) (shown) or by a percentage (%) of the maximum force applied during the test. The elapsed time represents the time dependence of the measurement during the test. The circles drawn at the base of the pulses represent the location for measuring the minimum applied force value for each pulse. This represents a "resting" applied force. The relative amplitude difference between successive minimum values represents the ΔF between the pulses' minimum values. This ΔF value describes the digit's ability to return to a smooth resting force profile.

This resting force is typically constant with the amplitude correlated to the physical position in which the hand sensor unit is held. By measuring the standard deviation of the differential minimum force, i.e., the difference between successive valleys, a measure of the resting force repeatability is obtained. For a normal uninjured hand, this force differential will be small and relatively uniform.

Figures 1, 13:
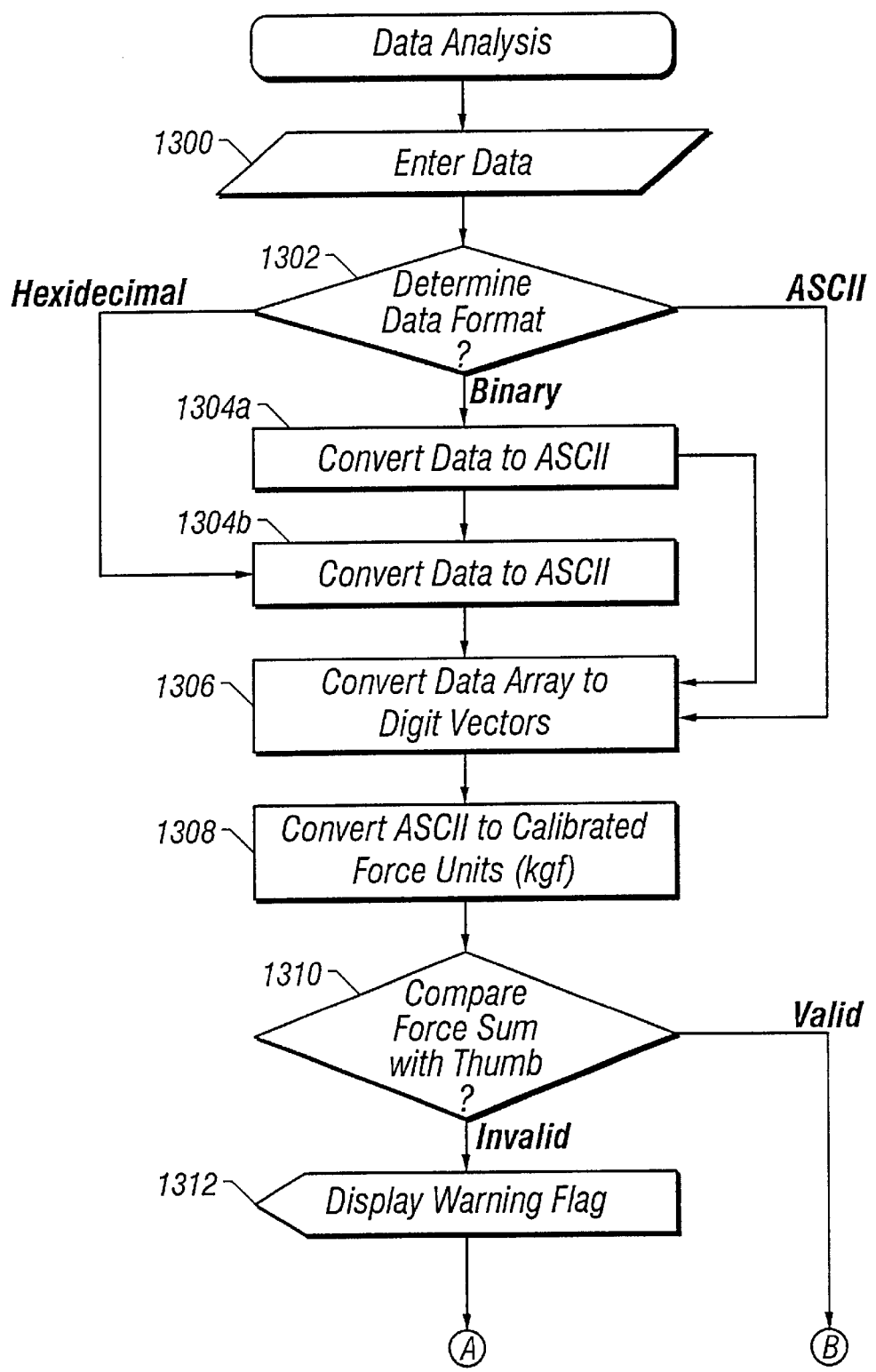
FIG. 13 is a computational flow diagram according to a preferred embodiment of the present invention.
Figures 2, 13:
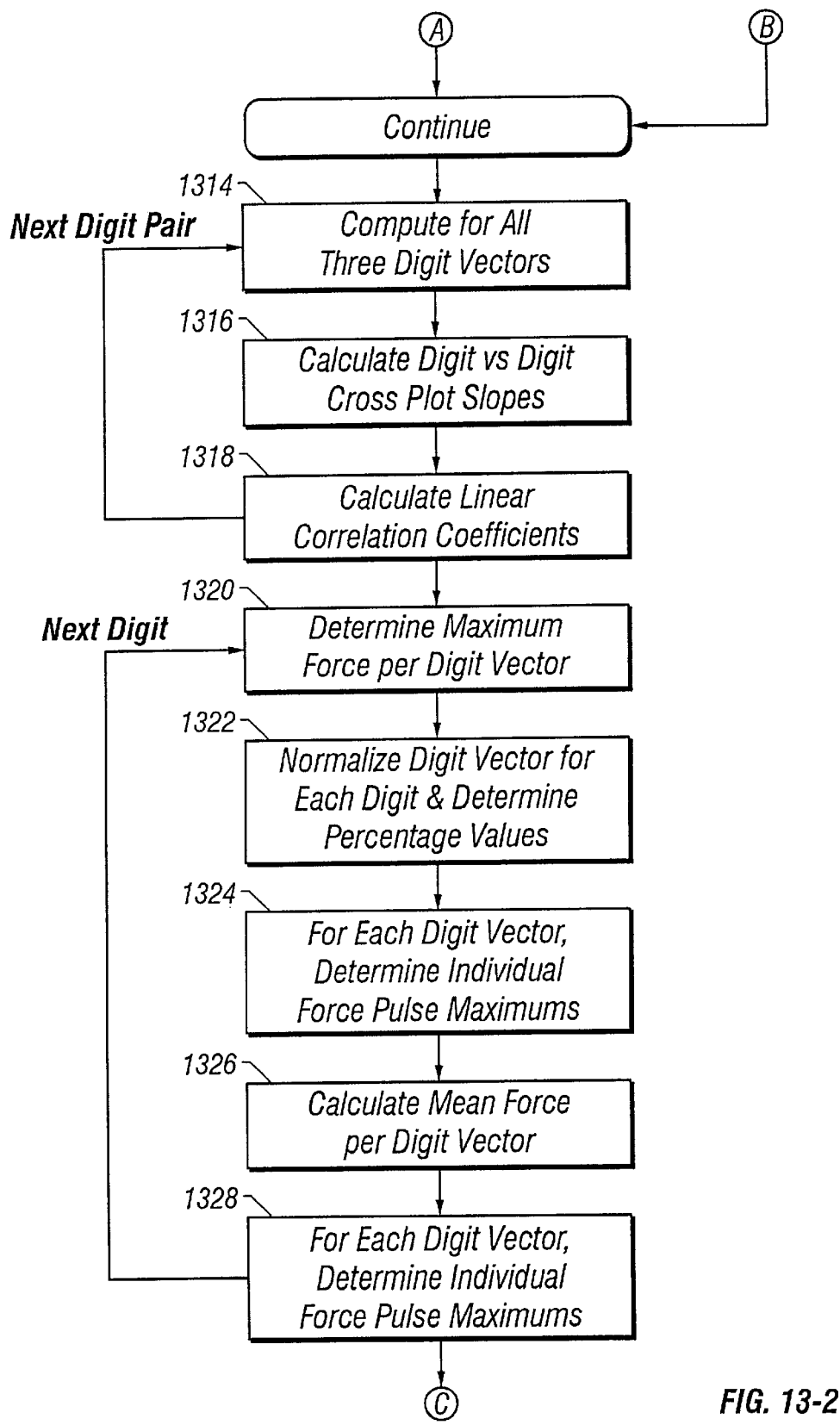
Figures 3, 13:
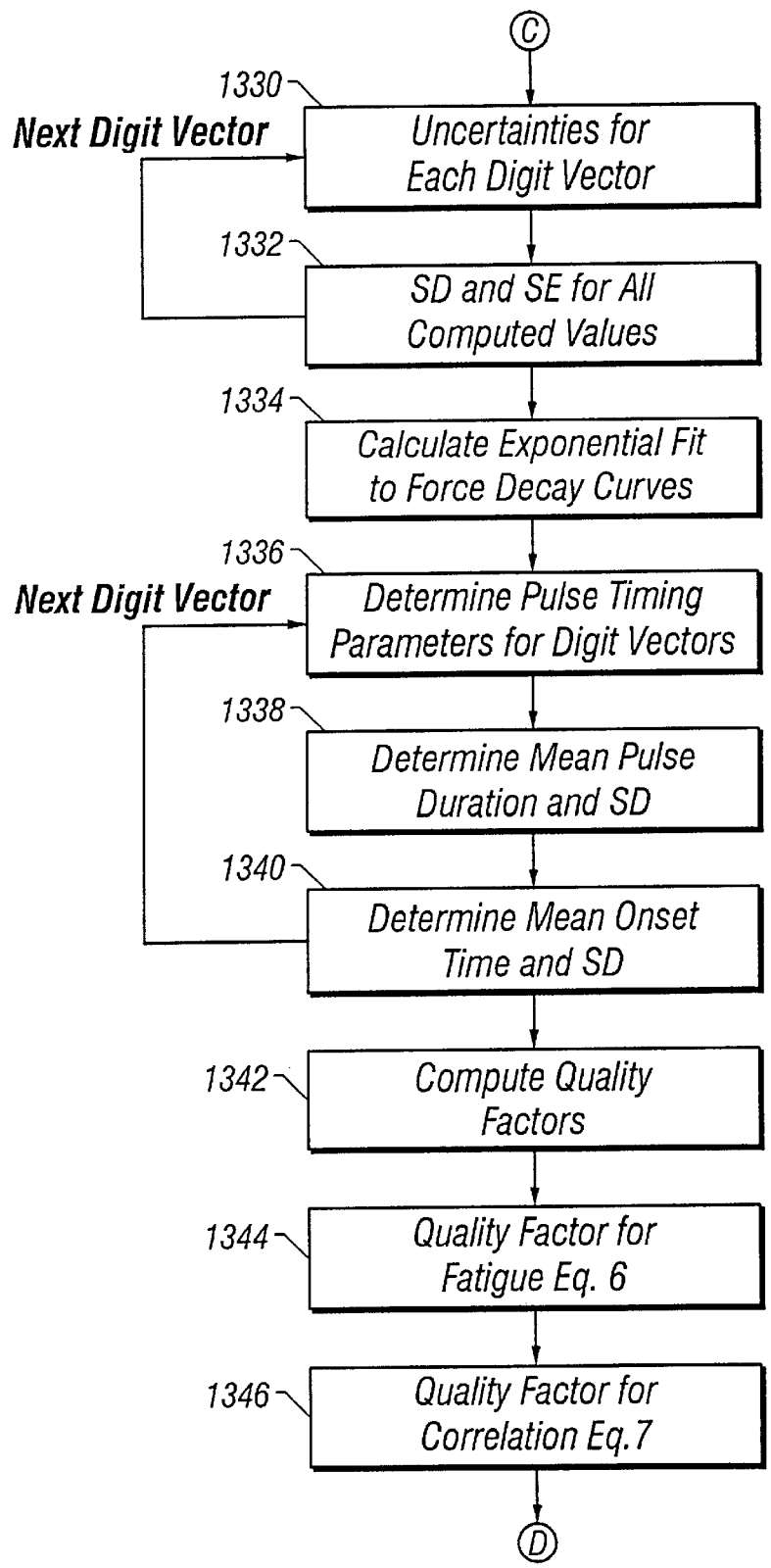
Figures 4, 13:
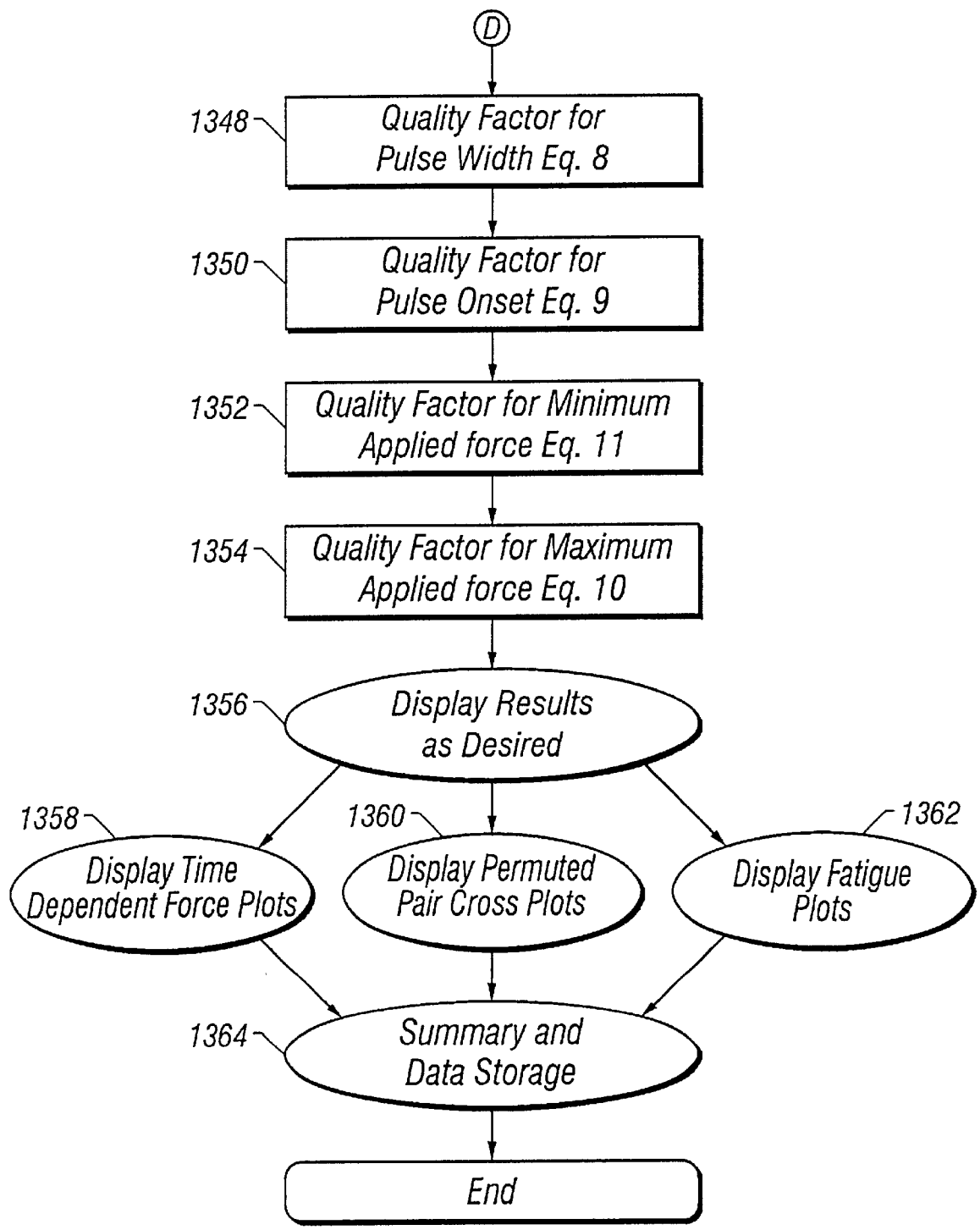

As will be clear to those of skill in the art, computation of the quality indices described herein may be facilitated by using an appropriately configured computer or processing system. For example, in a preferred embodiment of the present invention, computer 16 may process data according to the computational flow diagram shown in FIG. 13. As depicted in FIG. 13, this processing may comprise the following steps. Initially, data is entered into the computer by one of at least two means. Referring to FIG. 13, as shown in step 1300, previously collected and stored data may be entered into computer 16 as an array from a secondary computer or from a data storage device (e.g., 3¼ inch discs, zip discs, compact discs, or the like). As indicated in Step 1302, this data may be entered in ASCII format or may be read as a binary or hexadecimal file and converted to ASCII as indicated in steps 1404a and 1404b. Alternatively, the data also may be entered for "real time" analysis and display. The real time communication may be achieved by using any number of Windows® based industry standard methods, such as, but not limited to, Lab View™, or Visual Basic™, or C++ programming standards. Data also may be analyzed using non-Windows® based means, such as Fortran 77™ processing standards.

Figures 14, 15:
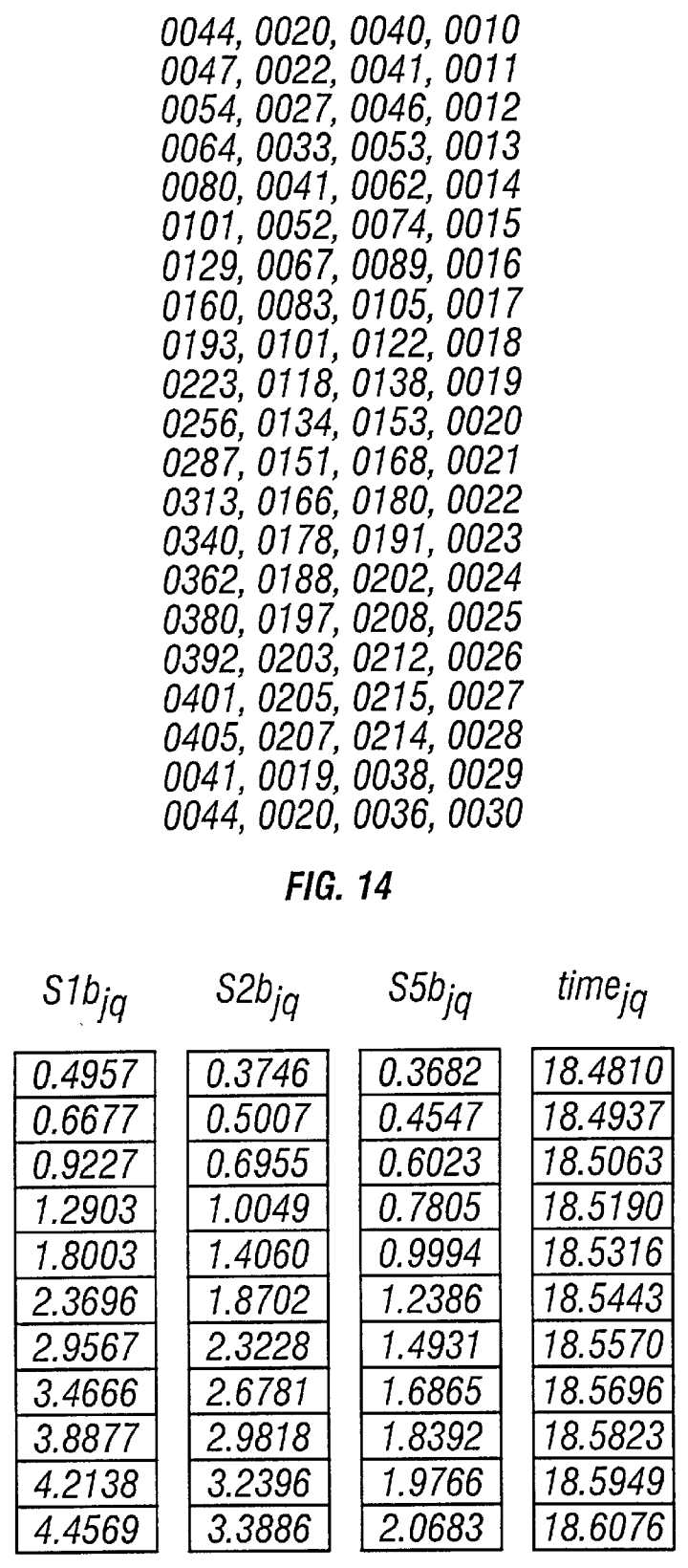

The data set may consist of an array, at least four columns wide by as many rows as are necessary to complete the test. The first column provides the force applied by the thumb (first digit), the second column lists the index finger (second digit) and the third column lists the small finger (fifth digit). The fourth column lists the elapsed time in scaled units. FIG. 14 depicts an example of a data array for part of a single pulse.

Figures 2B, 16:
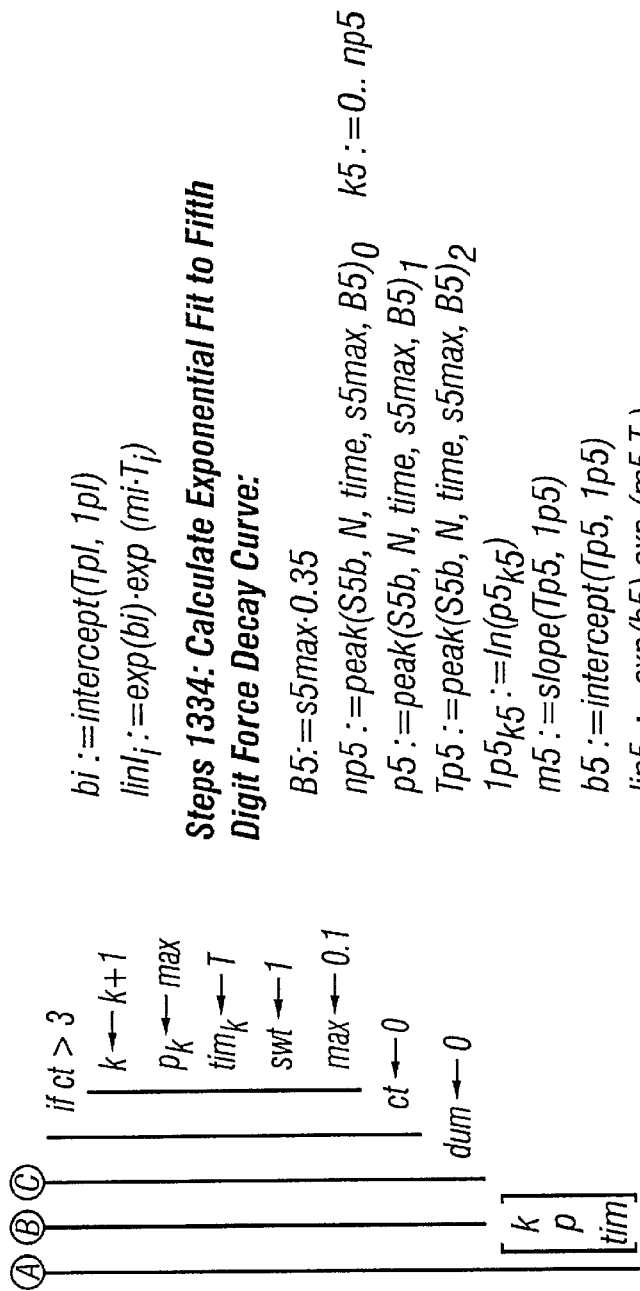
FIG. 16 is a sample MathCad computation according to a preferred embodiment of the present invention.
Figures 6A, 16:
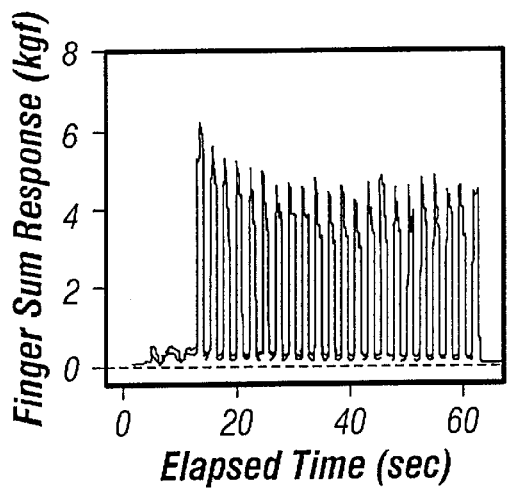
Figures 6B, 16:
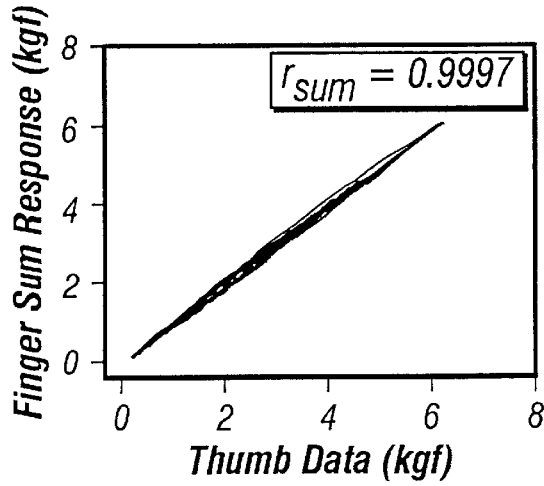
Figures 6C, 16:
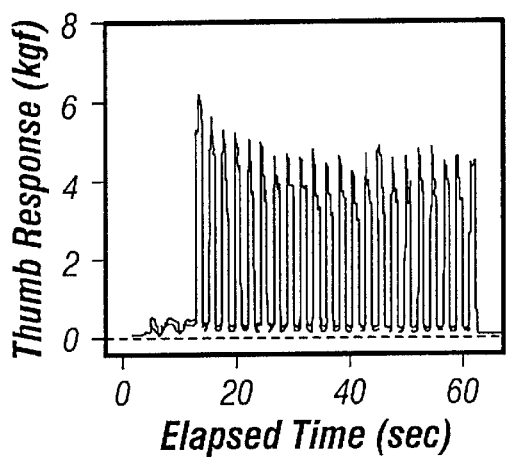
Figures 6D, 16:
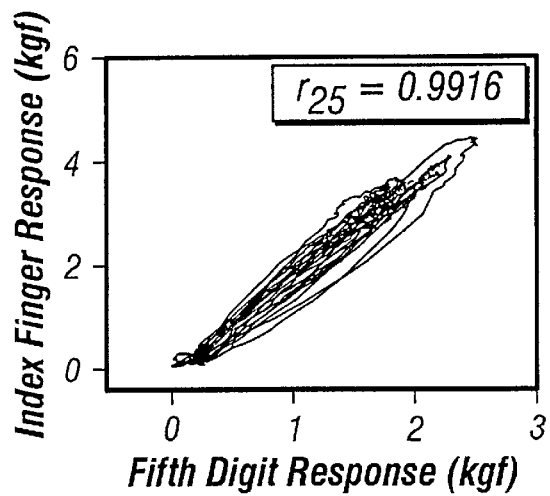
Figures 6E, 16:
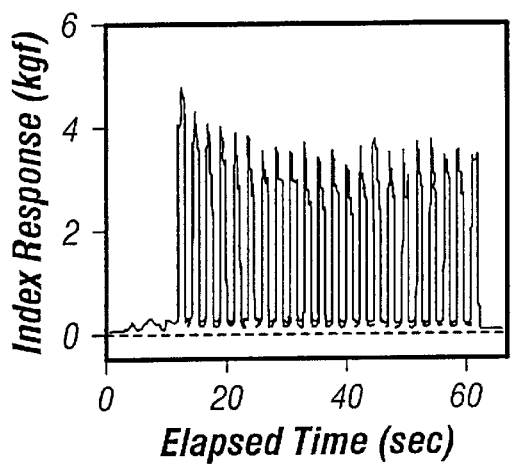
Figures 6F, 16:
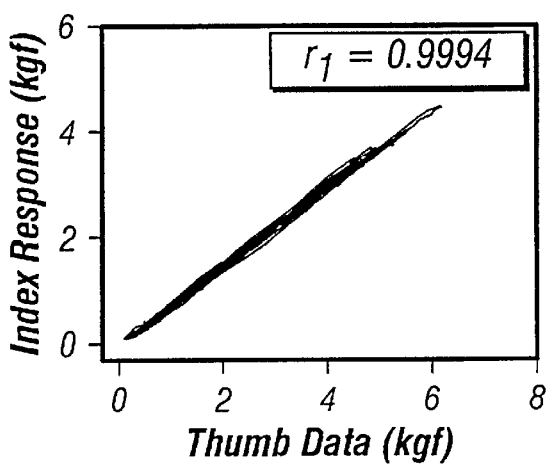
Figures 6G, 16:
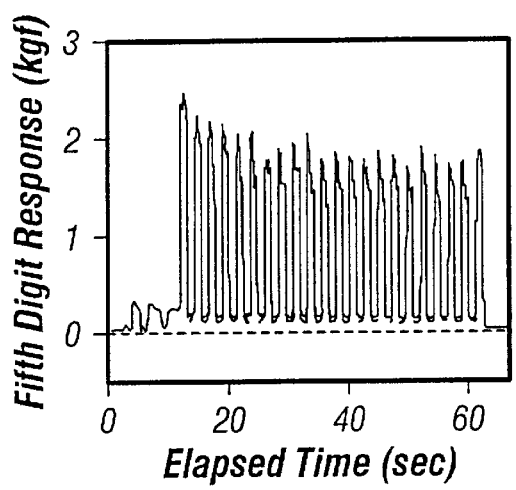
Figures 6H, 16:
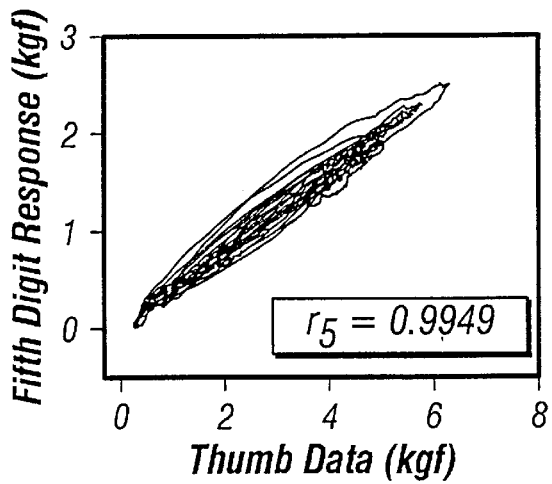
Figures 7A, 16:
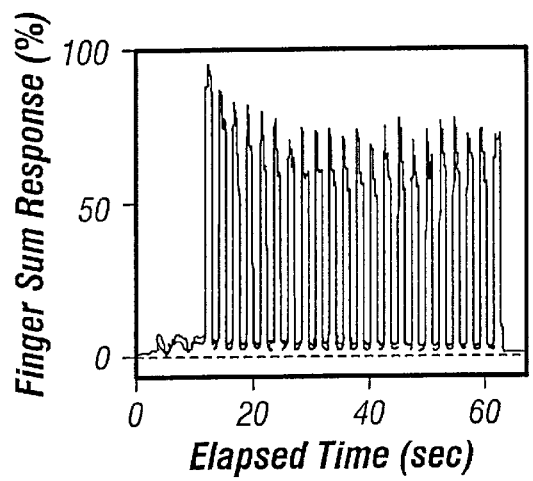
Figures 7B, 16:
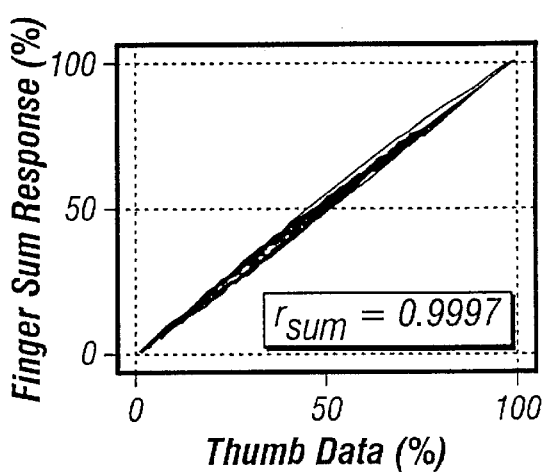
Figures 7C, 16:
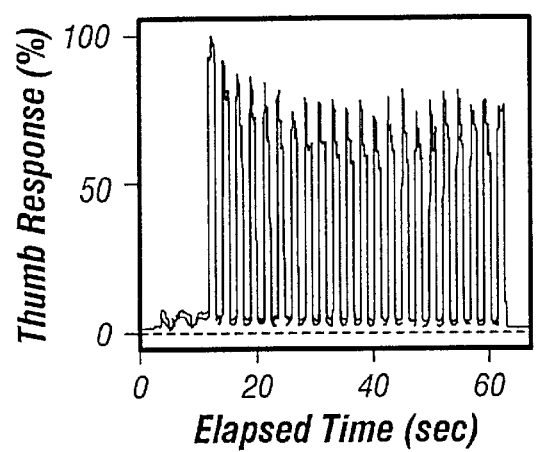
Figures 7D, 16:
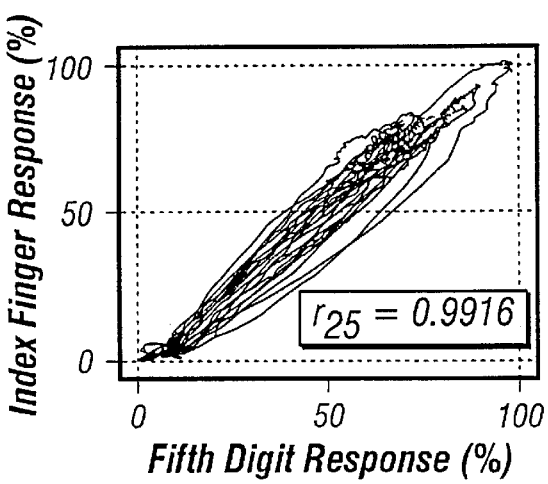
Figures 7E, 16:
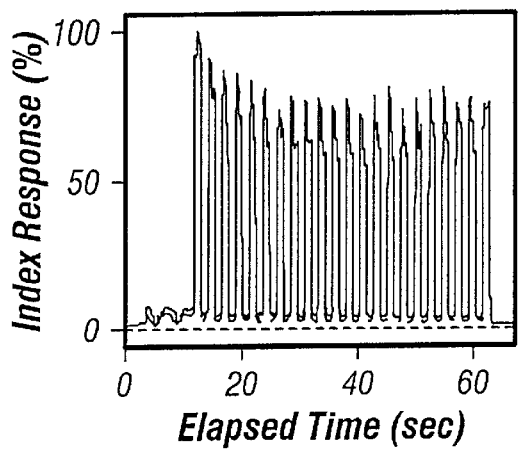
Figures 7F, 16:
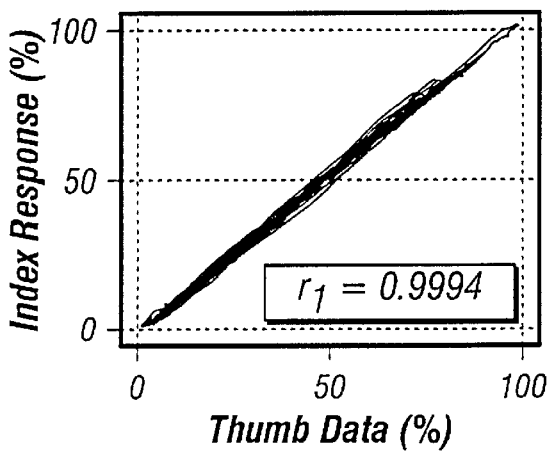
Figures 7G, 16:
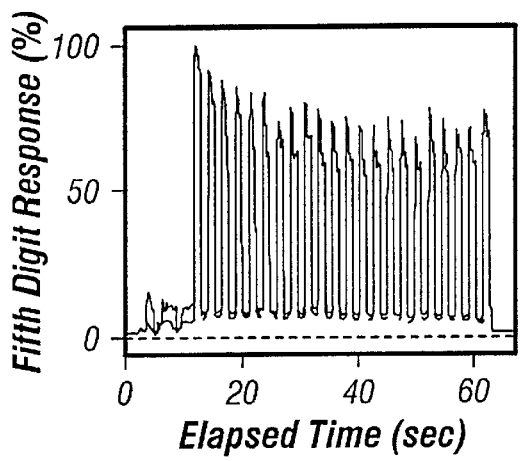
Figures 7H, 16:
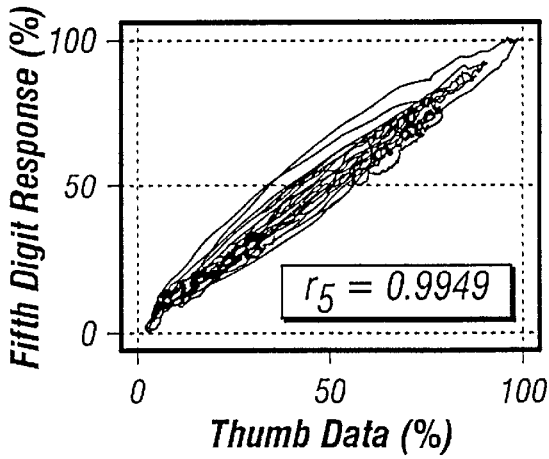
Figures 8A, 16:
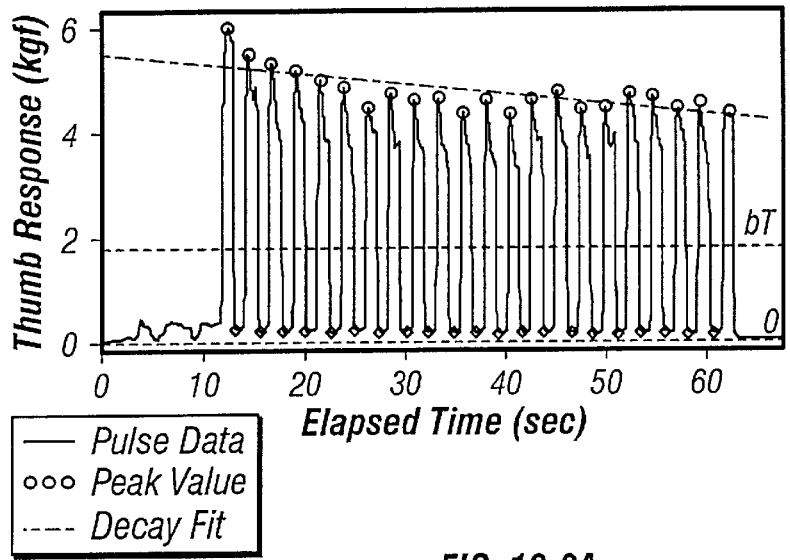
Figures 8B, 16:
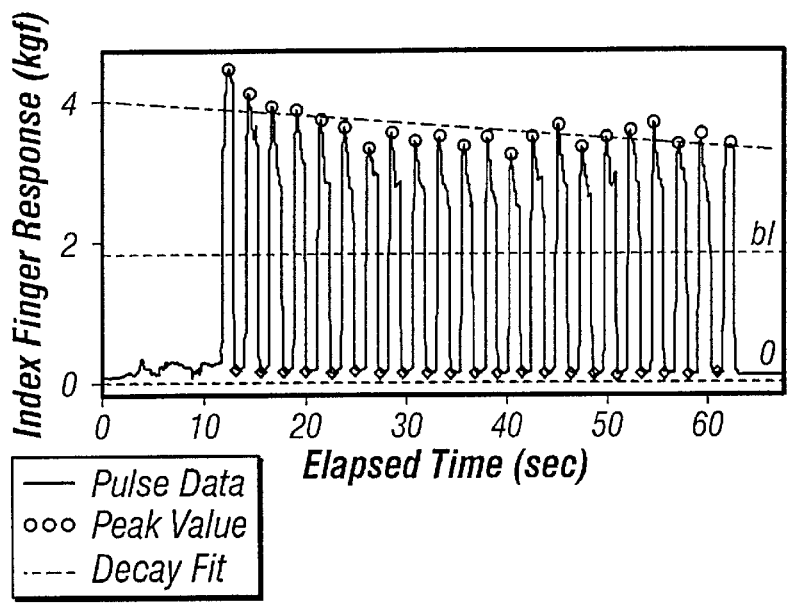
Figures 8C, 16:
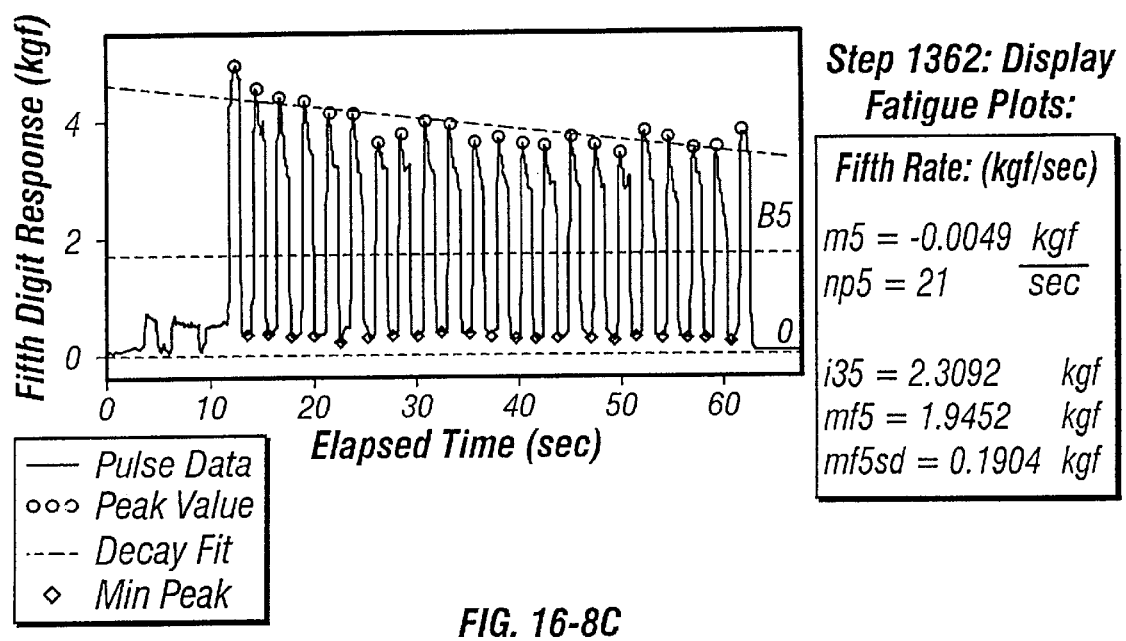
Figures 9B, 16:
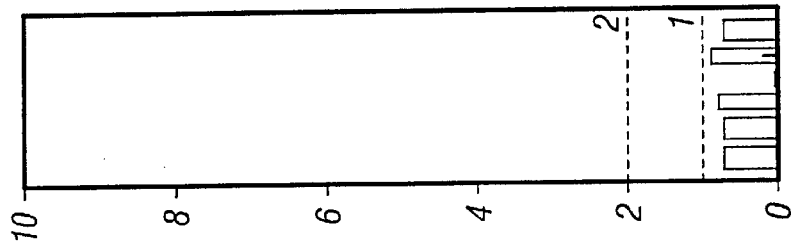

According to step 1306, the data array then is converted into vectors representing the applied uncalibrated forces as measured per unit sampling time for each digit measured and a fourth vector representing the elapsed time measured in seconds. Further, according to step 1308, the digit vectors are converted into calibrated forces measured in kgf (kilogram force) units. Referring to FIG. 15, a sample data set might look like following vectors which are taken from a MathCad data sheet. S1b represents the thumb (digit 1), S2b represents the index finger (digit 2) and S5b represents the small finger (digit 5). The time vector is listed in units of elapsed seconds, and the force vectors are listed in units of kgf. An example of MathCad computations according to a preferred embodiment of the invention is attached as FIG. 16.

Once converted, the validity of the collected data is checked by comparing the trigonometric sum of the finger forces (digits 2 and 5) to the force exerted by the thumb (digit 1), as described in step 1310. If the sum is not statistically close, i.e., within ±2 standard deviations), a flag (step 1312) warns the operator that invalid data is being or has been collected.

Referring to step 1314, the initial data analysis may comprise time dependent force analysis and permuted combinations of the digit's force cross plots. Thus, in step 1316, the three permuted cross plot slopes are computed from the data pairs: Digit 1 vs Digit 2; Digit 1 vs Digit 5, and Digit 2 vs Digit 5; and the quality check data set, e.g., the finger sum (Digits 2 and 5) vs the thumb (Digit 1). These four data sets will be referred to hereinafter, collectively, as the "permuted pairs." In step 1318, the analysis continues with the calculation of the Pearson linear correlation coefficient, r, for the permuted pairs. Steps 1314 through 1318 then are repeated for each digit pair.

If the correlation coefficient for the finger pair vs the thumb is too low (e.g., <0.995), a flag warns the operator that invalid data may exist. In step 1320, the maximum force exerted by each digit over the total elapsed time is computed. This maximum applied force then is used in step 1322 to normalize the data vector, so that in that same step, the percentage force applied throughout the data set may be determined. Referring to steps 1324 and 1328, the individual force pulses exerted by the separate digits are used to determine the maximum and minimum force per pulse, and the mean applied force over the entire elapsed time is determined in step 1326. Steps 1320 through 1328 are then repeated for each digit.

The statistical uncertainties are determined for each digit vector are determined in step 1330. In step 1332, the standard deviation (SD) and standard error (SE) are determined for all of the measured or computed parameters. Steps 1330 and 1332 are repeated for each digit. Subsequently, in step 1334, a non-linear exponential fit (e.g., by applying Eq.(3)) is made to plot the time dependent applied force data to determine the effective force decay rate, or "fatigue" for each of the digits. These values may be used to identify and assess subsequent improvements or declines in subject's hands at a later date.

Referring to step 1336, the individual pulse timing information is extracted from the data for each digit. The data then is used in step 1338 to determine the mean pulse duration width over the elapsed time. The uncertainties (SD and SE) are also determined for each mean pulse duration calculation In step 1340, the mean pulse onset time, i.e., time between applied force pulses, is calculated and the uncertainties noted. Steps 1336 through 1340 are then repeated for each digit vector.

The quality factors are computed in step 1342, based on all of the measured and computed parameters. In step 1344, the fatigue quality factor is computed using Eq. (6), described above. The linear correlation quality factor is then computed using Eq. (7), as indicated in step 1346. Subsequently, the pulse width quality factor is computed in step 1348 using Eq. (8); the pulse onset quality factor is computed in step 1350 using Eq. (9); the minimum or resting applied force quality factor is computed in step 1352 using Eq. (11); and the quality factor for the maximum applied pulse forces is computed in step 1354 using Eq. (10).

Selected results of the foregoing analysis may then be graphically displayed in step 1356. In particular, linear force vs time plots may be presented according to step 1358, for all data. Further, permuted pair cross-plots may be graphically depicted according to step 1360. Finally, the fatigue plots may be graphically depicted in step 1362. The exponential fit results also may be displayed for each series of plots to provide visual confirmation of valid analysis.

Ultimately, in step 1364, the results of the data analysis are stored, and a summary data sheet is provided to permit concise evaluation. All the measured and computed parameters, as well as their associated uncertainties, may be written to a data table to provide ease of reading. The quality factors may be presented in a bar plot form to permit a quick, visual scan to detect evidence of injury. Alternatively, the quality factors may be listed in a separate data table for quick reference.

Accordingly, one embodiment of the invention is directed to a method for qualitatively evaluating the digital performance of a person comprising the steps of measuring a first applied force as a function of time, the force being applied by the first digit of the hand (thumb) to a first force detector, to determine a first data set, measuring a second applied force as a function of time, the force being applied by a digit innervated by the median nerve to a second force detector, to determine a second data set, measuring a third applied force as a function of time, the force being applied by a digit innervated by the ulnar nerve to a third force detector, to determine a third data set, and cross-correlating or combining the first, second and third data sets to create or determine a patient digital performance profile.

The patient digital performance profile preferably comprises one or more quality indices, which indicate the presence or absence of injury. The quality indices evaluate the health of the hand and the innervation of the hand by comparing the relative performance of the median and ulnar nerve innervated digits with respect to each other.

The method may further comprise the step of comparing the patient digital performance profile to a plurality of predetermined diagnostic digital performance profiles, each of the diagnostic digital performance profiles corresponding to a particular disease. These predetermined diagnostic digital profiles may be compiled by comparing the profiles of a population of individuals having the same diagnosis or condition to determine performance data or profiles pathognomonic or typical for that condition. Such profiles may be compiled, for example, in connection with clinical trials where patient diagnosis has been confirmed using electrodiagnosis.

Alternately, the method may further comprise the step of comparing the patient digital performance profile to a previous or subsequent digital performance profile for the patient for the same or opposite hand.

Preferably, the first, second and third applied forces are measured during the same time interval. The first, second and third applied forces as a function of time may be selected from the group consisting of forces exerted by the digits during a sustained grip, during a plurality of repeated gripping and releasing motions, during a plurality of repeated gripping and releasing motions in response to a signal, and combinations of one or more thereof.

Another embodiment of the invention is directed to a method for qualitatively evaluating a digital performance of a person to detect disease comprising the steps of measuring a first applied force as a function of time, the force being applied by a thumb to a first force detector, to determine a first data set, measuring a second applied force as a function of time, the force being applied by a digit innervated by the median nerve to a second force detector, to determine a second data set, measuring a third applied force as a function of time, the force being applied by a digit innervated by the ulnar nerve to a third force detector, to determine a third data set, and substituting all or a portion of the first, second and third data sets into one or more quality index formulas to determine one or more patient quality indices, comparing the one or more patient quality indices to a plurality of predetermined diagnostic quality indices, each of the diagnostic quality indices having a value corresponding to a different disease, and detecting the presence of disease.

Different disease syndromes will have quality indices pathognomonic or typical for that particular condition. The patient's indices are compared to the different quality indices for each condition. If the patient's indices match or approximate the indices for a particular disease, a diagnosis may be made by the physician or other health care provider.

The step of detecting may be detecting the type or severity of disease. The first, second and third applied forces as a function of time may be selected from the group consisting of forces exerted by the digits during a sustained grip, during a plurality of repeated gripping and releasing motions, during a plurality of repeated gripping and releasing motions in response to a signal, and combinations of one or more thereof.

The one or more quality index formulas may be derived from Eq. (5) as set forth above. More specifically, the one or more quality index formulas may be selected from the group consisting of Eqs. (6–11), as set forth above.

In one embodiment of the method, the first, second and third applied forces comprise a force exerted by the respective digit during multiple pulses of gripping and releasing, and one of the one or more quality index formulas comprises a formula for calculating an applied force time dependent attenuation (decay) index, the formula comprising Eq. (6).

In another embodiment of the method, the first, second and third applied forces comprise a sustained force exerted by the respective digit during multiple pulses of gripping and releasing, and one of the one or more quality index formulas comprises a formula for calculating a linear correlation coefficient, the formula comprising Eq. (7).

In another embodiment of the method, the first, second and third applied forces comprise a force exerted by the respective digit during multiple pulses of attempted uniform gripping and releasing, and one of the one or more quality index formulas comprises a formula for calculating a pulse width uncertainty correlation coefficient, the formula comprising Eq. (8).

In another embodiment of the method, the first, second and third applied forces comprise a force exerted by the respective digit during multiple pulses of gripping and releasing in response to a stimulus, and one of the one or more quality index formulas comprises a formula for calculating a pulse onset correlation coefficient, the formula comprising Eq. (9).

In another embodiment of the method, the first, second and third applied forces comprise a maximum measured force exerted by the respective digit during multiple pulses of gripping and releasing, and one of the one or more quality index formulas comprises a formula for calculating a mean maximum applied force correlation coefficient, the formula comprising Eq. (10).

In another embodiment of the method, the first, second and third applied forces comprise a minimum applied force exerted by the respective digit during multiple pulses of gripping and releasing, and one of the one or more quality index formulas comprises a formula for calculating a mean minimum applied force correlation coefficient, the formula comprising Eq. (11).

Another embodiment of the invention is directed to a method for evaluating the digital performance of a person to detect disease comprising the steps of evaluating the relative strength, relative coordination and relative fatigue rates of a digit innervated by the median nerve and a digit innervated by the ulnar nerve to obtain a patient performance data set, and comparing the patient performance data set to a plurality of data sets characteristic of the digital performance of normal individuals and individuals suffering from different diseases in order to determine a disease status of the person.

The disease status may be the presence or absence of detectable disease. The detectable disease is selected from the group consisting of carpal tunnel syndrome, multiple sclerosis, ALS, Parkinson's disease, polio, thoracic outlet syndrome, or other diseases which may affect the hand.

Another embodiment of the invention is directed to a diagnostic profile library for diagnosing the presence or absence of disease in a patient based on a digital performance of a patient, comprising a plurality of diagnostic digital performance profiles, each of the diagnostic digital performance profiles correlating with the presence of a different disease, the diagnostic digital performance profiles determined by evaluating performance of a median nerve innervated digit and an ulnar nerve innervated digit for each of a plurality of persons having been diagnosed with each different disease, and determining the characteristics of the diagnostic performance profile correlatable with each different disease. The library of profiles may be embodied in written form or stored on magnetic tape or CD ROM.

Another embodiment of the invention is directed to a data base comprising a plurality of data sets as measured from a plurality of patients, the data sets each comprising measurements of the relative strength, relative coordination and relative fatigue rates of a digit innervated by the median nerve and a digit innervated by the ulnar nerve for each of the plurality of patients. After the data sets are gathered, they may be categorized based on the physical status of the patients. Data sets for individuals suffering from the same condition are evaluated and correlated using neural networks or other suitable methods to determine a profile typical of that particular disease or condition. The data sets are used to determine different profiles which may be cross-correlated with different identified physical conditions.

For example, persons with known CTS injuries have demonstrated the following patterns:
  Weakness in the index finger and thumb
  Rapid force decay (fatigue) in index finger and sometimes thumb
  Shift in grip force from thumb-index pair to thumb-fifth pair during testing
  Poor linear correlation between index and fifth digits
  Poor peak force amplitude control; peak force very erratic
  Poor resting force amplitude control; baseline very erratic
  Responsive to the onset cue tone, but timing delays exist between digital force exertion onset.

The above patterns lead to the following quality factor results.

The first three points cause the fatigue quality factor [$QI_D$; Eq. (6)] to become quite large due to the inevitable slope shift accompanying the dominant grip shift from the index to the fifth digit.
  The correlation factor [$QI_r$; Eq. (7)] increases rapidly as the index and fifth digits fail to grip coherently, as though they fail to cross communicate on the grip.
  The peak amplitude factor [$QI_{MF}$; Eq. (10)] increases quickly as the erratic nature of the peak applied force increases. Normal exponential decay curves are used to "normalize" the erratic nature of the variable. This normalization causes sign changes which exacerbate the poor results.

The baseline amplitude [$QI_{RF}$; Eq. (11)] (resting force amplitude) behaves the same way as the peak force, except that the normalization curve is a horizontal straight line. The erratic nature in the baseline force is not always present when the peak force is erratic.

Onset time variations [$QI_{po}$; Eq. (9)] between the digits reinforce the poor force correlation seen in the linear correlation factors. In addition, other injuries/diseases can cause these timing uncertainties.

Force duration time variations [$QI_{pw}$; Eq. (8)] lead to poor quality factors due to the increased spread in the "timing jitter," which the digits exhibit as they maintain a grip for the prescribed time.

The overall pattern of these factors allows differentiation between injured and non-injured hands. Hands without injury tend to exhibit quality factors less than one (1.00), while injured hands, specifically CTS injuries, tend to exhibit quality factors greater than two (2.00) and as large as ten (10.00) to twenty (20.00).

Another embodiment is directed to a data base such as an Internet web site, that allows for measurements of a patient's digital performance, for example, in a physician's office, to be analyzed remotely. The patient's measurements may be taken using an apparatus according to the present invention in any remote location, such as a doctor's office or other testing facility. The patient's data may be transmitted electronically, such as via a modem using the Internet, to a central data base site, such as a web site, for analysis. The data base preferably comprises means for receiving data from one or more remote locations, means for storing the data, and means for comparing the data to a plurality of data sets to determine a result. Preferably, the result is a differential diagnosis or alternately, a list of one or more physical conditions correlatable with the patient's data. The data base optionally comprises means for transmitting the results to the remote location. For example, the results may be transmitted electronically or in written form to the health care provider or any desired recipient.

In one embodiment of the invention a collection, transmission and reporting device is used in conjunction with a central analysis service. Test results are collected using a unit which comprises a hand held force sensor fixture as previously described and a monitor which communicates with a portable laptop computer. Test results or data are transmitted via modem to a central site, such as LabLink™ for analysis. The data are verified as valid and then analyzed at the central site. Electronic verification may be provided and a preliminary report may be sent electronically, i.e., within 24 hours, followed by a hard copy of the report via mail. Diagnostic code may be upgraded periodically as needed. Archives may be maintained to provide historical data and analysis of previous patient results.

Still another embodiment is directed to an apparatus for evaluating the digital performance of a person's hand to detect disease comprising a plurality of digit contact members for engagement with the digits of the hand, the plurality of digit contact members comprising a thumb contact member engageable by the thumb of the hand and a lateral digit contact member engageable by a lateral digit of the hand, the lateral digit being innervated in whole or in part by the ulnar nerve, a plurality of force detector means, the plurality of force detector means comprising a first force detector means operatively connected to the lateral digit contact member and a second force detector means operatively connected to a digit contact member engaged by a medial digit, the medial digit being innervated in whole or in part by the median nerve, each of the force detector means adapted to measure the quantity of force applied to the respective contact member and producing an output indicative of the quantity of force. Preferably, the first and second force detector means further comprise means for measuring force as a function of time. The apparatus may further comprise means for displaying the outputs.

The medial digit may be the thumb; in this embodiment, the second force detector means is operatively connected to the thumb contact member. Alternately, the medial digit may be the second digit; in this embodiment, the plurality of digit contact members further comprises a medial digit contact member and the second force detector means is operatively connected to the medial digit contact member. Alternately, the plurality of digit contact members may further comprise a medial digit contact member; in this embodiment, the second force detector means is operatively connected to the medial digit contact member and the plurality of force detector means further comprises a third force detector means operatively connected to the thumb contact member.

The lateral digit may be the fourth or fifth digit of the hand. The median nerve innervated digit may be the thumb, the second digit (index), the third digit or, less preferably, the fourth digit of the hand.

The apparatus may further comprise one or more of the following: means for measuring the relative strength of the digits being tested; means for measuring the absolute strength of the digits being tested; means for assessing relative coordination between the digits being tested; and means for measuring fatigue rate of the digits being tested.

Another embodiment of the invention is directed to a system for objective, repeatable, non-invasive analysis of a person's hand and/or wrist to determine the presence or absence of neural, muscular, soft tissue, bone or joint damage. This system comprises: three or more force members or contact members, one of which is engageable by the thumb of the person's hand and two of which are engageable by other digits, at least one of which is innervated by the ulnar nerve, and through which forces exerted in moving the thumb and other digits toward or away from each other in natural gripping and releasing motions may be transmitted; force detector means operatively connected to at least two of the contact members, one of which is engaged by an ulnar nerve innervated digit and one of which is engaged by a median nerve innervated digit, for measuring the quantity of force applied through the contact members by a respective thumb or other digit of the person's hand and for producing outputs indicative of the forces generated by the digits; and display means for displaying the outputs.

Preferably, the three or more contact members are operatively aligned in a fixture so that an engageable surface of each of the contact members is perpendicular to the force exerted thereto by its respectively engaging digit as the digits are moved toward or away from each other in the natural gripping and releasing motions of the person's hand. The contact members are preferably operatively aligned in the fixture so that the projection of forces transmitted through each of the contact members meet at a point between the contact members.

The contact members may be adjustable within the fixture to allow proper alignment of the contact members for persons of differing hand configuration and gripping and releasing motions. The contact members may be made of a rigid, relatively noncompressible material.

In this embodiment, the force detector means and the display means may be cooperatively connected to display the outputs in a time frequency related manner indicative of the forces generated by the digits during repetitive gripping and releasing motions of the person's hand. Alternately or additionally, the force detector means and the display means may be cooperatively connected to display the outputs in a time related manner indicative of the forces generated by the digits during the duration of prolonged gripping or releasing of the person's hand.

Preferably, a contact member is provided for each of the thumb, the second digit and the fifth digit of the person's hand, which is engageable by the pads of the fingertips of the respective digits. Preferably, these contact members are operatively aligned in a fixture so that the surface of each contact member engaged by the respective fingertip of the thumb or digit is perpendicular to the force exerted thereto by its respective the thumb or digit as the thumb and the second and fifth digits are moved toward each other in the natural gripping and releasing motions of the person's hand. The contact members may be operatively aligned in the fixture so that the projection of forces transmitted through each of the contact members meet at a point between the contact members. The contact members may be made adjustable within the fixture to allow proper alignment of the contact members for persons of differing hand configuration and gripping or releasing motions.

Preferably, the force detector means is operatively connected to the contact members for each of the thumb, second digit and fifth digit. The system may further include displacement measuring means operatively connected to one or more of the contact members for measuring the displacement of the one or more of the contact members as the thumb and other digits are moved toward or away from each other.

Another embodiment is directed to a non-invasive method of determining the presence or absence of neural, muscular, soft tissue, bone or joint damage to a person's hand and/or wrist, the method comprising the steps of: (a) having the person engage, with the pads of the tips of at least three digits of the hand, respective ones of three or more force transmitting members which are operatively aligned so that the surface of each of the force transmitting members is perpendicular to the force exerted thereto by its respectively engaging digit; (b) having the person move the digits toward or away from each other as the person closes or opens the hand in natural gripping and releasing motions; (c) measuring the force transmitted to at least two of the force transmitting members, one of which is engaged by a median nerve innervated digit and one of which is engaged by an ulnar nerve innervated digit, to provide quantifiable outputs therefor; and (d) displaying the quantifiable outputs representing the forces exerted by at least two digits innervated by differing nerves.

The person may keep the hand closed or opened for a prolonged period of time. Additionally or alternately, the person may move the hand in gripping and releasing motions.

The steps of measuring the forces and displaying the quantifiable outputs may be conducted in a manner to produce outputs in a time and/or frequency and/or phase related display. The quantifiable outputs may be processed by computer means for storage or immediate use.

The time and/or frequency and/or phase related outputs may be studied and used in diagnosis of specific hand, wrist and arm diseases or injuries using one or more of the following: pattern recognition, neural networks, frequency and/or phase analysis, signature analysis, plotting or graphic displays for visual analysis. The method may be repeated at hourly, daily, weekly, yearly or other desired intervals to determine long term effects of the diseases or injuries. Optionally, a visual or audible signal may be produced to indicate to the person when they should move the hand in the gripping and releasing motions.

The force transmitting members may be provided on an existing tool or instrument to allow relative force/displacement measurements to be made while the tool or instrument is being used in the normal way by the person. The ergometric design of the tool or instrument may be studied and optimized by selective placement of the force transmitting members on the tool or instrument to determine normalized forces on and displacement of the tool or instrument in actual use.

The devices and methods of the present invention are useful for detecting soft tissue disease, bone disease (including joint disease) or combinations thereof. For example, soft tissue diseases which may be evaluated include neural disease, muscular disease, connective tissue disease, or a combination thereof. The present invention can be used to distinguish diseases due to neural abnormalities or conditions including, but not limited to, multiple sclerosis, carpal tunnel syndrome, Parkinson's disease, ALS, or thoracic outlet syndrome.

The devices and methods of the present invention may also be used to predict when injury might occur. Multiple tests on a patient's hand may be performed over a period of time to monitor deterioration or improvement.

While the forgoing disclosure and description of the invention is illustrative and explanatory thereof, various changes in the method steps as well as the details of the illustrated preferred embodiment may be made without departing from the scope and spirit of the invention. Other embodiments and uses of the invention will be apparent to those skilled in the art from consideration of the specification and practice of the invention disclosed herein. All references cited herein, including all U.S. and foreign patents and patent applications, including U.S. patent application Ser. No. 09/041,775 filed Mar. 13, 1998, are specifically and entirely incorporated by reference. The specification and examples should be considered exemplary only with the true scope and spirit of the invention indicated by the following claims.

I claim:

1. A method for qualitatively evaluating a digital performance of a person comprising:
    measuring a first applied force as a function of time, said force being applied by a thumb to a first force detector, to determine a first data set;
    measuring a second applied force as a function of time, said force being applied by a digit innervated by the median nerve to a second force detector, to determine a second data set;
    measuring a third applied force as a function of time, said force being applied by a digit innervated by the ulnar nerve to a third force detector, to determine a third data set; and
    cross-correlating the first second and third data sets to create a patient digital performance profile.

2. The method of claim 1 wherein the patient digital performance profile comprises one or more quality indices.

3. The method of claim 2 wherein the quality indices indicate presence or absence of injury.

4. The method of claim 1 further comprising the step of comparing the patient digital performance profile to a plurality of diagnostic digital performance profiles, each of said diagnostic digital performance profiles corresponding to a different disease.

5. The method of claim 1 further comprising the step of comparing the patient digital performance profile to a previous digital performance profile for said patient for the same hand.

6. The method of claim 1 further comprising the step of comparing the patient digital performance profile to a subsequent digital performance profile for said patient for the same hand.

7. The method of claim 1 further comprising the step of comparing the patient digital performance profile to a digital performance profile for said patient for the opposite hand.

8. The method of claim 1 wherein the first, second and third applied forces are measured during the same time interval.

9. The method of claim 1 wherein said first, second and third applied forces as a function of time are selected from the group consisting of forces exerted by the digits during a sustained grip, during a plurality of repeated gripping and releasing motions, during a plurality of repeated gripping and releasing motions in response to a signal, and combinations of one or more thereof.

10. The method of claim 1 wherein the steps of measuring the first, second and third applied forces further comprise measuring displacement caused by the forces applied by the thumb, the digit innervated by the median nerve and the digit innervated by the ulnar nerve.

11. A method for qualitatively evaluating a digital performance of a person to detect disease comprising:

measuring a first applied force as a function of time, said force being applied by a thumb to a first force detector, to determine a first data set;

measuring a second applied force as a function of time, said force being applied by a digit innervated by the median nerve to a second force detector, to determine a second data set;

measuring a third applied force as a function of time, said force being applied by a digit innervated by the ulnar nerve to a third force detector, to determine a third data set;

substituting all or a portion of said first, second and third data sets into one or more quality index formulas to determine one or more patient quality indices; comparing the one or more patient quality indices to a plurality of diagnostic quality indices, each of said diagnostic quality indices corresponding to a different disease; and detecting the presence of disease.

12. The method of claim 11 wherein the step of detecting comprises detecting the type of disease.

13. The method of claim 11 wherein the step of detecting comprises detecting severity of disease.

14. The method of claim 11 wherein a said first, second and third applied forces as a function of time are selected from the group consisting of forces exerted by the digits during a sustained grip, during a plurality of repeated gripping and releasing motions, during a plurality of repeated gripping and releasing motions in response to a signal, and combinations of one or more thereof.

15. The method of claim 11 wherein said one or more quality index formulas are derived from the formula:

$$QI = c \cdot \left( \left( \frac{P_i - P_{i+1}}{P_i} \right)^j + \left( \frac{P_i - P_{i+2}}{P_i} \right)^j + \left( \frac{P_{i+1} - P_{i+2}}{P_i} \right)^j \right)^{\frac{1}{n}}$$

where:
QI=the quality index value,
c=multiplier chosen to normalize the quality index,
$p_i$=measured parameter for the first of the tested digits,
$p_{i+1}$=measured parameter for the second of the tested digits,
$p_{i+2}$=measured parameter for the third of the tested digits,
j=2, 4, 6 . . . , and
n=1, 2, 3 . . . .

16. The method of claim 15 wherein n=2 and c=1.

17. The method of claim 11 wherein said first, second and third applied forces comprise a force exerted by the respective digit during multiple pulses of gripping and releasing, and wherein one of said one or more quality index formulas comprises a formula for calculating an applied force time dependent attenuation (decay) index (QID), said formula comprising:

$$QI_D = c \cdot \left( \left( \frac{mt - mi}{mt} \right)^2 + \left( \frac{mt - m5}{mt} \right)^2 + \left( \frac{mi - m5}{mt} \right)^2 \right)^{\frac{1}{n}}$$

where:
c=the multiplier chosen to normalize the quality index,
mt=exponential decay slope of the first digit,
mi=exponential decay slope of the second digit,
m5=exponential decay slope of the fifth digit, and
n=1, 2, 3 . . . .

18. The method of claim 11 wherein said first, second and third applied forces comprise a sustained force exerted by the respective digit during multiple pulses of gripping and releasing, and wherein one of said one or more quality index formulas comprises a formula for calculating a linear correlation coefficient ($QI_r$), said formula comprising:

$$QI_r = c \cdot \left( \left( \frac{rit - r5t}{rit} \right)^2 + \left( \frac{ri5 - rit}{rit} \right)^2 + \left( \frac{ri5 - r5t}{rit} \right)^2 \right)^{\frac{1}{n}}$$

where:
c=the multiplier chosen to normalize the quality index,
rit=Pearson's linear correlation coefficient between the first digit and second digit,
r5t=Pearson's linear correlation coefficient between the first digit and fifth digit,
ri5=Pearson's linear correlation coefficient between the second digit and fifth digit, and
n=1, 2, 3 . . . .

19. The method of claim 11 wherein said first, second and third applied forces comprise a force exerted by the respective digit during multiple pulses of attempted uniform gripping and releasing, and wherein one of said one or more quality index formulas comprises a formula for calculating a pulse width uncertainty correlation coefficient ($QI_{pw}$, said formula comprising:

$$QI_{pw} = c \cdot$$

-continued $$\left(\left(\frac{sdwT-sdwI}{sdwT}\right)^2+\left(\frac{sdwT-sdw5}{sdwT}\right)^2+\left(\frac{sdwI-sdw5}{sdwT}\right)^2\right)^{\frac{1}{n}}$$

where:
c=the multiplier chosen to normalize the quality index,
sdwT=standard deviation of the full pulse width at half maximum for the first digit,
sdwI=standard deviation of the full pulse width at half maximum for the second digit,
sdw5=standard deviation of the full pulse width at half maximum for the fifth digit, and
n=1, 2, 3 . . . .

20. The method of claim 11 wherein said first, second and third applied forces comprise a force exerted by the respective digit during multiple pulses of gripping and releasing in response to a stimulus, and wherein one of said one or more quality index formulas comprises a formula for calculating a pulse onset correlation coefficient ($QI_{po}$), said formula comprising:

$$QI_{po}=c\cdot\left(\left(\frac{OtT-OtI}{OtT}\right)^2+\left(\frac{OtT-Ot5}{OtT}\right)^2+\left(\frac{Ot5-OtI}{OtT}\right)^2\right)^{\frac{1}{n}}$$

where:
c=the multiplier chosen to normalize the quality index,
OtT=standard deviation of the differential pulse onset time for the first digit,
OtI=standard deviation of the differential pulse onset time for the second digit,
Ot5=standard deviation of the differential pulse onset time for the fifth digit, and
n=1, 2, 3 . . . .

21. The method of claim 11 wherein said first, second and third applied forces comprise a maximum measured force exerted by the respective digit during multiple pulses of gripping and releasing, and wherein one of said one or more quality index formulas comprises a formula for calculating a mean maximum applied force correlation coefficient ($QI_{MF}$), said formula comprising:

$$QI_{MF}=c\cdot\left(\left(\frac{mfTsd-mfIsd}{mfTsd}\right)^2+\left(\frac{mfTsd-mf5sd}{mfTsd}\right)^2+\left(\frac{mf5sd-mfIsd}{mfTsd}\right)^2\right)^{\frac{1}{n}}$$

where:
c=the multiplier chosen to normalize the quality index,
mfTsd=standard deviation of the differential maximum applied force by the first digit,
mfIsd=standard deviation of the differential maximum applied force by the second digit,
mf5sd=standard deviation of the differential maximum applied force by the fifth digit, and
n=1, 2, 3 . . . .

22. The method of claim 11 wherein said first, second and third applied forces comprise a minimum applied force exerted by the respective digit during multiple pulses of gripping and releasing, and wherein one of said one or more quality index formulas comprises a formula for calculating a mean minimum applied force correlation coefficient, said formula comprising:

$$QI_{RF}=c\cdot\left(\left(\frac{mrTsd-mrIsd}{mrTsd}\right)^2+\left(\frac{mrTsd-mr5sd}{mrTsd}\right)^2+\left(\frac{mr5sd-mrIsd}{mrTsd}\right)^2\right)^{\frac{1}{n}}$$

where:
c=the multiplier chosen to normalize the quality index,
mrTsd=standard deviation of the differential resting applied force for the first digit,
mrIsd=standard deviation of the differential resting applied force for the second digit,
mr5sd=standard deviation of the differential resting applied force for the fifth digit, and
n=1, 2, 3 . . . .

23. A method for evaluating a digital performance of a person to detect disease comprising:
evaluating the relative strength, relative coordination and relative fatigue rates of a digit innervated by the median nerve and a digit innervated by the ulnar nerve to obtain a patient performance data set; and
comparing the patient performance data set to a plurality of data sets characteristic of the digital performance of normal individuals and individuals suffering from different diseases in order to determine a disease status of the person.

24. The method of claim 23 wherein the disease status is the presence or absence of detectable disease.

25. The method of claim 23 wherein the detectable disease is selected from the group consisting of carpal tunnel syndrome, multiple sclerosis, ALS, Parkinson's disease, polio and thoracic outlet syndrome.

26. A diagnostic profile library for diagnosing the presence or absence of disease in a patient based on a digital performance of a patient, comprising a plurality of diagnostic digital performance profiles, each of said diagnostic digital performance profiles correlating with the presence of a different disease, said diagnostic digital performance profiles determined by evaluating performance of a median nerve innervated digit and an ulnar nerve innervated digit for each of a plurality of persons having been diagnosed with said disease and determining the characteristics of the diagnostic performance profile correlatable with said disease.

27. A data base comprising a plurality of data sets as measured from a plurality of patients, said data sets each comprising measurements of the relative strength, relative coordination and relative fatigue rates of a digit innervated by the median nerve and a digit innervated by the ulnar nerve for each of said plurality of patients.

28. The data base of claim 27 wherein each data set is cross-correlated for an identified physical condition.

29. The data base of claim 27 wherein said data base further comprises means for receiving electronic data from at least one remote location, said data comprising a measurement of relative strength, relative coordination, and relative fatigue rates of a digit innervated by the median nerve and a digit innervated by the ulnar nerve of a patient; means for comparing the data to the plurality of data sets to determine a result, said result comprising one or more physical conditions correlatable with said data; and means for transmitting said result to said remote location.

30. An apparatus for evaluating the digital performance of a hand to detect disease comprising:
a plurality of digit contact members for engagement with the digits of the hand, said plurality of digit contact members comprising a thumb contact member engageable by the thumb of the hand and a lateral digit contact member engageable by a lateral digit of the hand, said lateral digit being innervated in whole or in part by the ulnar nerve;

a plurality of force detector means, said plurality of force detector means comprising a first force detector means operatively connected to the lateral digit contact member and a second force detector means operatively connected to a digit contact member engaged by a medial digit, said medial digit being innervated in whole or in part by the median nerve, each of said force detector means adapted to measure the quantity of force applied to the respective contact member and producing an output indicative of said quantity of force.

31. The apparatus of claim 30 wherein said first and second force detector means further comprise means for measuring force as a function of time.

32. The apparatus of claim 30 wherein said medial digit is the thumb and said second force detector means is operatively connected to the thumb contact member.

33. The apparatus of claim 30 wherein said medial digit is the second digit and said plurality of digit contact members further comprises a medial digit contact member and wherein said second force detector means is operatively connected to said medial digit contact member.

34. The apparatus of claim 30 wherein said plurality of digit contact members further comprises a medial digit contact member and wherein said second force detector means is operatively connected to said medial digit contact member and wherein said plurality of force detector means further comprises a third force detector means operatively connected to said thumb contact member.

35. The apparatus of claim 30 wherein said lateral digit is the fourth or fifth digit of the hand.

36. The apparatus of claim 30 wherein said median nerve innervated digit is the thumb, the second digit, the third digit or the fourth digit of the hand.

37. The apparatus of claim 30 further comprising means for displaying said outputs.

38. The apparatus of claim 30 further comprising means for measuring the relative strength of the lateral digit and the medial digit.

39. The apparatus of claim 30 further comprising means for measuring the absolute strength of the lateral digit and the medial digit.

40. The apparatus of claim 30 further comprising means for assessing relative coordination between the lateral digit and the medial digit.

41. The apparatus of claim 30 further comprising means for measuring fatigue rate of the lateral digit and the medial digit.

42. The apparatus of claim 30 wherein said disease is soft tissue disease, bone disease or a combination thereof.

43. The apparatus of claim 30 wherein said soft tissue disease is selected from the group consisting of neural disease, muscular disease, connective tissue disease, or a combination thereof.

44. The apparatus of claim 30 wherein said neural disease is selected from the group consisting of multiple sclerosis, carpal tunnel syndrome, ALS, Parkinson's disease, polio or thoracic outlet syndrome.

45. The apparatus of claim 30 wherein said each of said force detector means is adapted to measure displacement caused by the force exerted by its respective digit.

* * * * *